(12) United States Patent
Prinz et al.

(10) Patent No.: US 12,297,346 B2
(45) Date of Patent: *May 13, 2025

(54) HYDROGEL COMPOSITION COMPRISING A CROSSLINKED POLYMER

(71) Applicant: CROMA-PHARMA GMBH, Leobendorf (AT)

(72) Inventors: Martin Prinz, Klosterneuburg (AT); Ralph Hollaus, Vienna (AT); Robert Sachsenhofer, Vienna (AT)

(73) Assignee: CROMA-PHARMA GMBH, Leobendorf (AT)

( * ) Notice: Subject to any disclaimer, the term of this patent is extended or adjusted under 35 U.S.C. 154(b) by 1148 days.

This patent is subject to a terminal disclaimer.

(21) Appl. No.: 17/252,542

(22) PCT Filed: Jun. 14, 2019

(86) PCT No.: PCT/EP2019/065754
§ 371 (c)(1),
(2) Date: Dec. 15, 2020

(87) PCT Pub. No.: WO2019/238953
PCT Pub. Date: Dec. 19, 2019

(65) Prior Publication Data
US 2021/0261760 A1    Aug. 26, 2021

(30) Foreign Application Priority Data
Jun. 15, 2018 (EP) .................................. 18178097

(51) Int. Cl.
*A61K 31/167* (2006.01)
*A61L 27/20* (2006.01)
(Continued)

(52) U.S. Cl.
CPC .............. *C08L 5/08* (2013.01); *A61K 31/167* (2013.01); *A61L 27/20* (2013.01); *A61L 27/26* (2013.01);
(Continued)

(58) Field of Classification Search
CPC .................................................... A61K 31/167
See application file for complete search history.

(56) References Cited

U.S. PATENT DOCUMENTS 4,582,865 A    4/1986  Balazs et al.
6,884,788 B2   4/2005  Bulpitt et al.
(Continued)

FOREIGN PATENT DOCUMENTS

CA    2348842 A1    5/2000
CA    2673323 A1    7/2008
(Continued)

OTHER PUBLICATIONS

Bernkop-Schnürch, A. and T. E. Hopf (2001). "Synthesis and in Vitro Evaluation of Chitosan-Thioglycolic Acid Conjugates." *Scientia Pharmazeutica* 69: 109-118.
(Continued)

*Primary Examiner* — Benjamin J Packard
(74) *Attorney, Agent, or Firm* — Workman Nydegger

(57) ABSTRACT

A sterile hydrogel composition that includes a crosslinked polymer, wherein the crosslinked polymer is an oxidation product of a thiol-modified hyaluronan and wherein the thiol-modified hyaluronan has a degree of modification of hyaluronan with thiol moieties of more than about 80 μmol per gram polymer, wherein the thiol-modified hyaluronan has a degree of modification of hyaluronan with thiol moieties of less than about 280 μmol per gram polymer, and wherein the thiol-modified hyaluronan has a mean molecular weight of at least 400 kDa.

22 Claims, 1 Drawing Sheet

(51) Int. Cl.
   *A61L 27/26* (2006.01)
   *A61L 27/52* (2006.01)
   *A61L 27/54* (2006.01)
   *A61M 5/32* (2006.01)
   *C08L 5/08* (2006.01)

(52) U.S. Cl.
   CPC ............... *A61L 27/52* (2013.01); *A61L 27/54* (2013.01); *A61M 5/329* (2013.01); *A61M 5/3295* (2013.01); *A61L 2300/204* (2013.01); *A61L 2300/402* (2013.01); *A61L 2400/06* (2013.01); *A61L 2430/34* (2013.01)

(56) References Cited

U.S. PATENT DOCUMENTS

| | | |
|---|---|---|
| 2002/0071855 A1 | 6/2002 | Sadozai et al. |
| 2004/0059066 A1 | 3/2004 | Yamamoto |
| 2008/0025950 A1 | 1/2008 | Prestwich et al. |
| 2008/0221062 A1 | 9/2008 | Miyamoto et al. |
| 2008/0292703 A1 | 11/2008 | Renier et al. |
| 2009/0093414 A1 | 4/2009 | Ikeya et al. |
| 2009/0155314 A1 | 6/2009 | Tezel et al. |
| 2009/0269417 A1 | 10/2009 | Gonzalez et al. |
| 2010/0028399 A1 | 2/2010 | Hornof |
| 2010/0316683 A1 | 12/2010 | Piron et al. |
| 2011/0038938 A1 | 2/2011 | Ison et al. |
| 2011/0038939 A1 | 2/2011 | Lvov et al. |
| 2012/0034271 A1 | 2/2012 | Shu |
| 2013/0123210 A1 | 5/2013 | Liu et al. |
| 2013/0210760 A1 | 8/2013 | Liu et al. |
| 2016/0038396 A1 | 2/2016 | Tezel |
| 2016/0220729 A1 | 8/2016 | Gousse et al. |
| 2016/0263147 A1 | 9/2016 | Shu et al. |
| 2019/0270829 A1 | 9/2019 | Zeng et al. |

FOREIGN PATENT DOCUMENTS

| | | |
|---|---|---|
| CN | 101367884 A | 2/2009 |
| CN | 101721349 | 6/2010 |
| CN | 104892962 | 9/2015 |
| CN | 107412002 | 12/2017 |
| EA | 013877 | 8/2008 |
| EP | 0587715 A1 | 3/1994 |
| EP | 1115433 B1 | 12/2004 |
| EP | 1790665 A1 | 5/2007 |
| EP | 2103631 A1 | 9/2009 |
| EP | 2614828 | 7/2013 |
| JP | 2010-512859 A | 4/2010 |
| JP | 2012521270 | 9/2012 |
| JP | 2013-537050 A | 9/2013 |
| WO | 92/20349 A1 | 11/1992 |
| WO | WO2003080135 | 10/2003 |
| WO | 2002056914 A1 | 5/2004 |
| WO | WO2004037164 | 5/2004 |
| WO | WO2005056608 | 6/2005 |
| WO | 2008/008857 A2 | 1/2008 |
| WO | 2005095464 A1 | 2/2008 |
| WO | WO 2008077172 | 7/2008 |
| WO | 2008148071 | 12/2008 |
| WO | WO 2009005790 | 1/2009 |
| WO | WO2009108100 | 9/2009 |
| WO | 2010111161 | 9/2010 |
| WO | WO2012167079 | 12/2012 |
| WO | WO2013086024 | 6/2013 |
| WO | 2014/064632 A1 | 5/2014 |
| WO | WO2014181147 | 11/2014 |
| WO | WO2016005785 | 1/2016 |
| WO | 2018/083326 A1 | 5/2018 |
| WO | 2019/238954 A1 | 12/2019 |

OTHER PUBLICATIONS

Bernkop-Schnürch, A., C. E. Kast and M. F. Richter (2001). "Improvement in the mucoadhesive properties of alginate by the covalent attachment of cysteine." *J Control Release* 71(3): 277-285.

Bernkop-Schnürch, A., V. Schwarz and S. Steininger (1999). "Polymers with thiol groups: a new generation of mucoadhesive polymers?" *Pharm Res* 16(6): 876-881.

Bernkop-Schnürch, A. (2005). "Thiomers: a new generation of mucoadhesive polymers." *Adv Drug Deliv Rev* 57(11): 1569-1582.

Kast, C. E. and A. Bernkop-Schnurch (2001). "Thiolated polymers—thiomers: development and in vitro evaluation of chitosan-thioglycolic acid conjugates." *Biomaterials* 22(17): 2345-2352.

Kast, C. E. and A. Bernkop-Schnurch (2002). "Polymer-cysteamine conjugates: new mucoadhesive excipients for drug delivery?" *Int J Pharm* 234(1-2): 91-99.

Krauland, A. H., M. H. Hoffer and A. Bernkop-Schnurch (2005). "Viscoelastic properties of a new in situ gelling thiolated chitosan conjugate." *Drug Dev Ind Pharm* 31(9): 885-893.

Marschütz, M. K. and A. Bernkop-Schnürch (2002). "Thiolated polymers: self-crosslinking properties of thiolated 450 kDa poly(acrylic acid) and their influence on mucoadhesion." *European Journal of Pharmaceutical Sciences* 15(4): 387-394.

Palmberger, T. F., K. Albrecht, B. Loretz and A. Bernkop-Schnürch (2007). "Thiolated polymers: Evaluation of the influence of the amount of covalently attached l-cysteine to poly(acrylic acid)." *European Journal of Pharmaceutics and Biopharmaceutics* 66(3): 405-412.

Perera, G., J. Hombach and A. Bernkop-Schnurch (2010). "Hydrophobic thiolation of pectin with 4-aminothiophenol: synthesis and in vitro characterization." *AAPS PharmSciTech* 11(1): 174-180.

Ågerup, B., P. Berg and C. Åkermark (2005). "Non-Animal Stabilized Hyaluronic Acid." *BioDrugs* 19(1): 23-30.

Bae, H. D., L. J. Yanke, K. J. Cheng and L. B. Selinger (1999). "A novel staining method for detecting phytase activity." *J Microbiol Methods* 39(1): 17-22.

Beasley, K. L., M.A. Weiss, R. A. Weiss (2009). "Hyaluronic acid fillers: a comprehensive review." *Facial Plast Surg* 25:86-94.

Bothner, H., T. Waaler and O. Wik (1988). "Limiting viscosity number and weight average molecular weight of hyaluronate samples produced by heat degradation." *International Journal of Biological Macromolecules* 10(5): 287-291.

Choi, J.-i., J.-K. Kim, J.-H. Kim, D.-K. Kweon and J.-W. Lee (2010). "Degradation of hyaluronic acid powder by electron beam irradiation, gamma ray irradiation, microwave irradiation and thermal treatment: A comparative study." *Carbohydrate Polymers* 79(4): 1080-1085.

Edsman, K., Å. Öhrlund, C. Sturesson, L. Nord, A. H. Kenne and J. Näsström (2010). The Difference Between Stabilization and Crosslinking. *8th Anti-aging Medicine World Congress (AMWC)*. Monaco.

Jones, D. S. (2009). Chitosan. *Handbook of Pharmaceutical Excipients Sixth Edition*. R. C. Rowe, P. J. Sheskey and M. E. Quinn. London Chicago, Pharmaceutical Press: 159-161.

Liu, N., L. Shao, X. Xu, J. Chen, H. Song, Q. He, Z. Lin, L. Zhang and C. B. Underhill (2002). "Hyaluronan metabolism in rat tail skin following blockage of the lymphatic circulation." *Lymphology* 35(1): 15-22.

Liu, Y., X. Zheng Shu and G. D. Prestwich (2005). "Biocompatibility and stability of disulfide-crosslinked hyaluronan films." *Biomaterials* 26(23): 4737-4746.

Lowry, K. M. and E. M. Beavers (1994). "Thermal stability of sodium hyaluronate in aqueous solution." *J Biomed Mater Res* 28(10): 1239-1244.

Mason, C., P. Dunnhill (2008). "A brief definition of regenerative medicine." *Regen Med* 3(1):1-5.

May, B. C., A. T. Fafarman, S. B. Hong, M. Rogers, L. W. Deady, S. B. Prusiner and F. E. Cohen (2003). "Potent inhibition of scrapie prion replication in cultured cells by Bis-acridines." *Proc Natl Acad Sci U S A* 100(6): 3416-3421.

Peppas, N. A. (1991). "Physiologically Responsive Hydrogels." *Journal of Bioactive and Compatible Polymers* 6(3): 241-246.

Prestwich, G. D., D. M. Marecak, J. F. Marecek, K. P. Vercruysse and M. R. Ziebell (1998). "Controlled chemical modification of

(56) References Cited

OTHER PUBLICATIONS hyaluronic acid: synthesis, applications, and biodegradation of hydrazide derivatives." *Journal of Controlled Release* 53(1): 93-103.
Quinn, M. E. and P. J. Sheskey (2009). Sodium Hyaluronate. *Handbook of Pharmaceutical Excipients Sixth Edition*. R. C. Rowe, P. J. Sheskey and M. E. Quinn. London Chicago, Pharmaceutical Press: 646-648.
Serban, M. A., G. Yang and G. D. Prestwich (2008). "Synthesis, characterization and chondroprotective properties of a hyaluronan thioethyl ether derivative." Biomaterials 29(10): 1388-1399.
Shu, X. Z., Y. Liu, Y. Luo, M. C. Roberts and G. D. Prestwich (2002). "Disulfide cross-linked hyaluronan hydrogels." Biomacromolecules 3(6): 1304-1311.
Shu, X. Z., Y. Liu, F. Palumbo and G. D. Prestwich (2003). "Disulfide-crosslinked hyaluronan-gelatin hydrogel films: a covalent mimic of the extracellular matrix for in vitro cell growth." *Biomaterials* 24(21): 3825-3834.
Sparer, R. V., N. Ekwuribe and A. G. Walton (1983). Controlled Release from Glycosaminoglycan Drug Complexes. *Controlled Release Delivery Systems*. T. J. Roseman and S. Z. Mansdorf. New York and Basel, Marcel Dekker, Inc.
*The international pharmacopoeia* [ *electronic resource*]—9th ed. (2019). Methods of sterilization. Geneva, World Health Organization.
Aufort et al., "Oxorhenium-Mediated Assembly of Noncyclic Selective Integrin Antagonists: A Combinatorial Approach", ChemBioChem, vol. 12, Issue 4, 2011, pp. 583-592.
Bernuzzi et al., "An innovative way to thermally sterilize hyaluronic acid pre-filled syringes", 2016 white paper available under https://demo6.esoul.it/wp-content/uploads/2019/07/WP_Thermal_Sterilization_PFS_with_Hyaluronic_Acid.pdf.
Borke et al., "Optimized triazine-mediated amidation for efficient and controlled functionalization of hyaluronic acid", Carbohydrate Polymers, vol. 116, 2015, pp. 42-50.
Boulle et al., "A review of the metabolism of 1,4-butanediol diglycidyl ether-crosslinked hyaluronic acid dermal fillers", Dermatol. Surg., vol. 39, No. 12, 2013, pp. 1758-1766.
Choi et al., "Modulation of biomechanical properties of hyaluronic acid hydrogels by crosslinking agents", J. Biomed. Mater Res. Part A, vol. 103, No. 9, 2015, pp. 3072-3080.
Cowman M.K. et al., "Improved agarose gel electrophoresis method and molecular mass calculation for high molecular mass hyaluronan," Analytical Biochemistry, vol. 417, 2011, pp. 50-56.
Griesser et al., "Thiolated Hyaluronic Acid as Versatile Mucoadhesive Polymer: From the Chemistry Behind to Product Developments—What Are the Capabilities?", Polymers, vol. 10, No. 3, 2018, 16 Pages.
Hoet P. H.M. et al., "Polyamines in the lung: polyamine uptake and polyamine-linked pathological or toxicological conditions," Am. J. Physiol. Lung Cell. Mol. Physiol, vol. 278, 2000, pp. L417-L433.
Liang et al., "Investigating triazine-based modification of hyaluronan using statistical designs", Carbohydrate Polymers, vol. 132, Issue 5, 2015, pp. 472-480.
Lim, "Hyaluronic acid filler injections with a 31-gauge insulin syringe, Australasian Journal of Dermatology", vol. 51, No. 1, 2010, pp. 74-75.
Monslow et al., "Hyaluronan—a functional and structural sweet spot in the tissue microenvironment," Frontiers in Immunology, vol. 6, No. 231, 2015, 19 Pages.
Naor, "Editorial: Interaction Between Hyaluronic Acid and Its Receptors (CD44, Rhamm) Regulates the Activity of Inflammation and Cancer, Frontiers in Immunology", vol. 7, No. 39, 2016, 4 Pages.
Shu et al., "Disulfide cross-linked hyaluronan hydrogels", Biomacromolecules, vol. 3, No. 6, 2002, pp. 1304-1311.
Stern et al., "The many ways to cleave hyaluronan", Biotechnology Advances, vol. 25, No. 6, 2007, pp. 537-557.
Stocks D. et al., "Rheological Evaluation of the Physical Properties of Hyaluronic Acid Dermal Fillers," J Drugs Dermatol, vol. 10, Issue 9, 2011, pp. 974-980.
Tokita et al., "Degradation of hyaluronic acid-Kinetic study and thermodynamics", Eur. Polym. J., vol. 32, No. 8, 1996, pp. 1011-1014.
Troncoso et al., "A kinetic study of the degradation of hyaluronic acid at high concentrations of sodium hydroxide", student thesis, 2016.
Shu et al., "Synthesis and evaluation of injectable, in situ crosslinkable synthetic extracellular matrices for tissue engineering", Journal of Biomedical Materials Research Part A, Dec. 15, 2006, pp. 902-912.
La Gatta, A. et al., 2016, ,Biophysical and biological characterization of a new line of hyaluronan-based dermal fillers: A scientific rationale to specific clinical indications, Materials Science and Engineering C 68: 565-572.
Shu, X. Z., S. Ahmad, Y. Liu, and G. D. Prestwich (2006). "Synthesis and evaluation of injectable, in situ crosslinkable synthetic extracelluar matrices for tissue engineering." J Biomed Mater Res A 79(4): 902-12.
Kafedjiiski, et al, "Synthesis and in vitro evaluation of thiolated hyaluronic acid for mucoadhesive drug delivery" International Journal of Pharmaceutics, Eslevier, NL vol. 343, No. 1-2, Aug. 30, 2007.
International Search Report issued in PCT/EP2019/065754, dated Sep. 20, 2019.
Cowman et al., "Improved agarose gel electrophoresis method and molecular mass calculation for high molecular mass hyaluronan, Analytical Biochemistry", vol. 417, No. 1, 2011, pp. 50-56.
Hoet et al., "Polyamines in the lung: polyamine uptake and polyamine-linked pathological or toxicological conditions", Am. J. Physiol. Lung Cell. Mol. Physiol., vol. 278, No. 3, 2000, pp. L417-L433.
International Search Report and Written Opinion received for PCT Patent Application No. PCT/EP2020/087140, mailed on Apr. 26, 2021, 11 pages.
International Search Report issued in PCT/EP2019/065755 mailed Sep. 19, 2019.
International Search Report issued in PCT/EP2019/065756 mailed Oct. 1, 2019.
Kafedjiiski, et al., "Synthesis and in vitro evaluation of thiolated hyaluronic acid for mucoadhesive drug delivery", International Journal of Pharmaceutics, Elsevier, NL, Vo. 343, No. 1-2, Aug. 30, 2007.
Stocks et al., "Rheological evaluation of the physical properties of hyaluronic acid dermal fillers", J. Drugs Dermatol., vol. 10, No. 9, 2011, pp. 974-980.
The international pharmacogoeia [electronic resource]—9th ed. (2019). Methods of sterilization. Geneva, World Health Organization.
Bian et al., The self-crosslinking smart hyaluronic acid hydrogels as injectable three-dimensional scaffolds for cells culture, Jan. 6, 2016, Colloids and Surfaces B: Biointerfaces, vol. 140, pp. 392-402. (Year: 2016).
Vanderhooft et al., "Rheological Properties of Cross-Linked Hyaluronan-Gelatin Hydrogels for Tissue Engineering", Macromolecular Journals, (2009), p. 20-28.
Ding et al., Multilayered mucoadhesive hydrogel films based on thiolated hyaluronic acid and polyvinylalcohol for insulin delivery, Acta Biomaterialia, vol. 8, pp. 3643-3651. (Year: 2012).

HYDROGEL COMPOSITION COMPRISING A CROSSLINKED POLYMER

The present invention relates to a sterile hydrogel composition, comprising a crosslinked polymer, wherein the crosslinked polymer is an oxidation product of a thiol-modified hyaluronan, as well as uses thereof and a method for producing the same.

STATE OF THE ART

Hyaluronan, abbreviated HA, also called hyaluronic acid and its salts, e.g. sodium hyaluronate, is a naturally occurring anionic, non-sulfated glycosaminoglycan with repeating disaccharides being composed of D-glucuronic acid and N-acetyl-D-glucosamine.

High molecular weight hyaluronan is naturally present in the skin and is known for its viscoelastic properties and also for its very high propensity to absorb water. Its properties contribute to a large extent to the elasticity of the skin. Given its properties and its qualities of biocompatibility, tolerance and lack of toxicity, advantage has thus been taken of this compound for more than 10 years now in many applications in the medical and cosmetics fields, in particular aesthetic procedures. For instance, hyaluronan is used for filling wrinkles via direct injection into the dermis in the area under consideration (use as dermal filler).

Highly purified unmodified HA of biofermentative origin is perfectly biocompatible and identical to endogenous hyaluronan. However, despite having the advantage of being highly compatible with the tissues of the human body, having a high affinity for water and performing a strong moisturising function, HA does not have adequate biomechanical properties. When HA is injected into skin tissues, there is a rapid in vivo degradation by both hyaluronidases (enzymatic degradation) and free radicals (chemical degradation) present in the tissues of the human body.

Numerous solutions have been proposed to slow down the in vivo degradation of HA and to modify its chemical, physical, and biological properties, additionally providing increased resistance of the formulations to degradation during storage, to heat and therefore to sterilization.

These approaches typically involve chemical modification of HA including for example crosslinking of HA by chemical, enzymatic or photochemical means. These crosslinked hyaluronan gels can be obtained by various preparation processes. Generally, these processes require two main steps, the first consisting of hydrating hyaluronan in order to convert it into an aqueous solution (hydrogel) and the second aimed at crosslinking the HA molecules of said aqueous solution in the presence of an agent capable of inducing the crosslinking thereof (also referred to as "crosslinking agent"). Examples of crosslinking agents include formaldehyde, divinyl sulfone, biscarbodiimides, and epoxides.

For the production of dermal fillers, the crosslinking agent is most commonly chosen from epoxides, such as 1,4-butanediol diglycidyl ether (BDDE) or 1,2,7,8-diepoxyoctane (DEO), aldehydes, or poly vinylsulfones, such as divinylsulfone (DVS), and is therefore synthetic in nature.

Unfortunately, chemical modifications lead to side effects and foreign body reactions not observed with unmodified HA, which has naturally low immunogenicity and no toxicity. In the majority of marketed HA soft tissue fillers BDDE is used as a crosslinking agent. Due to the reactive nature of the epoxide groups present in BDDE, non-reacted BDDE remaining in the dermal filler might have genotoxic effects. Thus, BDDE in dermal fillers has to be maintained at trace amounts (<2 parts per million), so that expensive additional purification and test procedures are needed during production. Although the safety profile of BDDE crosslinked fillers is supported by long term clinical experience (De Boulle, Glogau et al., 2013, A review of the metabolism of 1,4-butanediol diglycidyl ether-crosslinked hyaluronic acid dermal fillers, Dermatol Surg (39): 1758-1766), BDDE may still raise some safety concerns (Choi, Yoo et al., 2015, Modulation of biomechanical properties of hyaluronic acid hydrogels by crosslinking agents, J Biomed Mater Res Part A (103A): 3072-3080).

Due to the genotoxic risks associated with BDDE, the yearly dose of dermal filler products such as Juvederm®, which may be applied over the lifetime of a patient, is limited to 20 mL per year. Administration of the commercially available dermal filler product Restylane® is limited to a volume of 6 mL per application. Similar limitations apply to dermal fillers comprising DVS crosslinked hyaluronan.

Another problem with chemical modifications is the necessity of harsh reaction conditions, such as alkaline pH values and high temperatures (above 50° C.) to which hyaluronan has to be subjected during the crosslinking reaction in order to achieve the desired degree of crosslinking. It is known that the molecular weight of HA decreases because of hydrolytic degradation during exposure to acidic (pH below 4) or alkaline pH (pH above 10). In addition, hyaluronan is degraded at higher temperatures above 40° C. (Troncoso et al., 2016, A kinetic study of the degradation of Hyaluronic acid at high concentrations of sodium hydroxide, student thesis, accessed online via diva-portal.org/smash/get/diva2: 954372/FULLTEXT01.pdf; Stern et al., 2007. The many ways to cleave hyaluronan, Biotechnology Advances (25): 537-557; Tokita and Okamoto, 1996, Degradation of hyaluronic acid-kinetic study and thermodynamics, Eur. Polym. J. (32): 1011-1014). It is further known that low molecular weight hyaluronan fragments with a molecular weight of less than about 200 kDa have pro-inflammatory effects (Naor, 2016, Editorial: Interaction Between Hyaluronic Acid and Its Receptors (CD44, RHAMM) Regulates the Activity of Inflammation and Cancer, Frontiers in immunology 7:39; Monslow et al., 2015, Hyaluronan-a functional and structural sweet spot in the tissue microenvironment, Frontiers in immunology 6:231).

Disulfide cross-linked hyaluronan hydrogels were first described by Shu et al. (Biomacromolecules 3, 1304-1311, 2002).

The disulfide crosslinked derivative of a thiol-modified hyaluronan (HA-SH) may be obtained by a self-crosslinking mechanism. A network of crosslinked hyaluronan polymers establishes upon formation of disulfide bonds between thiol groups (HA-S-S-HA). The thiol group forming a disulfide bond may connect the pendant groups of a common HA backbone molecule or a neighbouring HA molecule, i.e. the crosslinking may be intramolecular or intermolecular, respectively. The formation of disulfide bonds from free thiol groups is an oxidation reaction that may occur spontaneously, e.g. due to ubiquitous oxygen, or upon addition of an oxidation agent.

WO 2004/037164 further studied hyaluronan modified with 3,3'-dithiobis(propanoic dihydrazide) (DTP) or 4,4'-dithiobis(butyric dihydrazide) (DTB). Gels obtained by disulfide formation and use of thiol reactive agents such as polyethylenglycol di(meth)acrylic acids for crosslinking were evaluated for their potential in tissue engineering, i.e. as a scaffold for growth and culture of cells for implantation.

In WO 2005/056608 the same techniques were employed to crosslink a thiolated hydrazide modified carboxymethyl hyaluronan to obtain macromolecular cell scaffolds. Serban et al. describe the synthesis of a 2-thioethyl ether hyaluronan derivative (Biomaterials 29, 1388-1399; 2008), which however was unsuitable for crosslinking by the investigated crosslinking agents. EP 2 103 631 describes thiol-modified macromolecules including hyaluronic acid, wherein a thiol group is introduced by a hydrazide coupling method, and its cross-linked products. The crosslinked products are either obtained with a crosslinking agent or by disulfide formation.

The synthesis of thiolated hyaluronic acid was also described in Kafedjiiski et al. (Int J Pharm 343, 48-58; 2007) as well as its potential use in drug delivery, wound healing and tissue repair. CN101367884A discloses the synthesis of HA-cysteamine conjugates which comprise both free thiol groups and disulfide groups. EP 2 614 828 describes thiol-modified biocompatible polymer derivatives with a low degree of modification and cross-linked materials thereof. WO 2008/077172 describes thiolated hyaluronic acid for tissue augmentation. In one example, WO 2008/077172 describes an intradermal application of a sterile hydrogel formulation with 2 g thiol-group containing hyaluronic acid (thiol-modified hyaluronan), wherein a depot formed by the thiol-group containing hyaluronic acid could be tactually detectable over two weeks; however, the document is silent about the specific features of the thiol-modified hyaluronan used in this example.

It is common knowledge that hyaluronan-based soft tissue fillers with a high elasticity (also described as stiffness or thickness), which comprise highly crosslinked hyaluronan and/or large particles and/or are made of high molecular weight hyaluronan and/or contain crosslinked hyaluronan in a high concentration, tend to last longer in the body (up to 6 months and more). Soft tissue fillers with high stiffness (elasticity) are successfully used to correct areas on the face like nasolabial folds, for restoring facial volume and shaping the contours of the face, to correct deeper wrinkles and folds, and in the treatment, for instance, of facial lipoatrophy, debilitating scars or morphological asymmetry. These soft tissue fillers are injected subcutaneously, supraperiosteally or into deep dermis. Injection of a "stiff" hydrogel with high elasticity generally requires a needle with a higher lumen, i.e. a thicker needle characterized by lower gauge values (for instance, 21 G, 23 G or 26 G).

It is also generally accepted that hyaluronan-based soft tissue fillers have a short residence time in the body if they show one or more of the following features:
  low viscosity and/or low elasticity,
  no or only moderate degree of crosslinking,
  no or only small particles,
  low molecular weight hyaluronan
  crosslinked hyaluronan in low concentration.

At the same time, these relatively "smooth" low viscosity hydrogels can be injected through thin needles, i.e. needles having high gauge values (such as 27 G to 32 G). The treatment of fine lines, wrinkles and superficial skin defects in sensitive skin areas (such as the periorbital region, the vulvovaginal region, the perioral region, and the lips) or in entire skin regions (such as the back of the hand) requires the use of a "smooth" dermal filler product to avoid the formation of lumps or bumps in these regions. Since multiple small volume injections may be required to obtain results, the hydrogel should be easy to inject through a thin needle (e.g. 29 G, 30 G or 32 G needle) to minimize patient discomfort, bleeding and bruising (Lim, Adrian C., Hyaluronic acid filler injections with a 31-gauge insulin syringe, *Australasian Journal of Dermatology* (2010) 51, 74-75).

Because of the short duration of effect current injectable treatment options for improving the appearance of fine lines require multiple treatment sessions (for example, 3 treatment sessions at 3-week intervals or 2 treatment sessions at 4-week intervals followed by maintenance treatments every 2 months). It has proven difficult to develop hyaluronan-based soft tissue fillers which are both easy to inject through a high gauge needle (i.e. thin needle) and which have an extended duration in the body.

The inventors of the present invention studied the potential of self-crosslinked thiol-modified hyaluronan as soft tissue fillers. However, initial in vivo studies with hydrogel formulations based on self-crosslinked thiol-modified hyaluronan showed short residence times of the implants of less than two months. Similar findings were made when testing two commercially available dermal filler products for fine line treatment.

Accordingly, it is an object of the present invention to provide a composition comprising a crosslinked polymer, wherein the crosslinked polymer is an oxidation product of a thiol-modified hyaluronan, which has improved properties especially regarding the application as smooth soft tissue filler, which is injectable through a thin needle.

SHORT DESCRIPTION OF THE INVENTION

The present invention provides a sterile hydrogel composition comprising a crosslinked polymer,
  wherein the crosslinked polymer is an oxidation product of a thiol-modified hyaluronan,
  wherein the thiol-modified hyaluronan has a degree of modification with thiol groups of more than about 80 µmol per gram polymer, preferably more than about 105 µmol per gram polymer, more preferably more than about 120 µmol per gram polymer,
  wherein the thiol-modified hyaluronan has a degree of modification with thiol groups of less than about 280 µmol per gram polymer, preferably less than about 240 per gram polymer, more preferably less than 200 µmol per gram polymer and
  wherein the thiol-modified hyaluronan has a mean molecular weight (MMW) of at least about 400 kDa, preferably at least about 500 kDa, more preferably at least about 600 kDa.

The sterile hydrogel composition according to the present invention is a hydrogel based on a modified hyaluronan with thiol groups (HA-SH), wherein the hyaluronan is cross-linked by disulfide bonds between the thiol groups of the modified hyaluronan (oxidation product of a thiol-modified hyaluronan). The oxidation product is a copolymer consisting of sections of unmodified hyaluronan and of modified hyaluronan, the latter being connected via disulfide bonds. The hydrogel is free of any additional external bifunctional crosslinking agents, such as divinyl sulfone. The hydrogel composition is characterized by comprising an oxidation product of a thiol-modified hyaluronan with an initial degree of modification between about 80 µmol thiol groups per gram polymer to about 280 µmol thiol groups per gram polymer.

The inventors found that the degree of modification of hyaluronan with thiol groups is an important feature for influencing the in vivo residence time of the sterile hydrogel. For soft tissue fillers is it desired that the implanted hydrogel remains at the site of implantation over an extended time period and thus, achieves a sustainable effect due to slow degradation. The hydrogel compositions comprising a crosslinked thiol-modified hyaluronan act as a soft tissue filler for an extended duration, for example, for at least about 3 months, after only a single treatment session, thereby eliminating the need for multiple repeated treatments to maintain the duration of effect.

Studies characterizing the in vivo performance of sterile hydrogel compositions are exemplified in Examples 8 and 9 below. The depot volume in % relative to the starting point is calculated to compensate for potential differences in the application volume. The depot volume at t=0 (directly after implantation) corresponds to 100%. The depot volume may be monitored for example via magnet resonance imaging (MRI) scans. It will be understood that the depot volume as biological parameter, preferably determined in animal models, is subject to great individual variation. Accordingly individual data points are less informative and only mean values (considering multiple application sites and/or multiple study objects) give conclusive data. Of course, the performance will further depend on factors such as the tissue type at the site of implantation, the used method for measuring the depot volume and the species of the studied organism. The quantitative transferability of the data, e.g. for application in humans, may be restricted. However, results comparable to the data in rats were observed in another in vivo study with mice (data not shown). Thus, the in vivo characterisation provides a valuable tool for assessing and comparing individual hydrogel compositions against each other. Residence time may be used as a parameter to describe the presence of a detectable depot during a period of time, preferably the presence of a mean relative depot volume of about 50% (or even more) during a time period. Preferably, the relative depot volume of about 50% (or more) is detectable during the first 3 to 4 weeks after a single application, more preferably up to 3 months and more. The hydrogel compositions according to the invention showed a residence time of 7 weeks (measured at day 52) post-injection under the exemplified study conditions. Thus, the hydrogel compositions according to invention show the desired in vivo performance promising for an applicability as soft tissue filler, e.g. in humans. Moreover, the nature of the crosslinked polymer provides a favourable toxicological safety profile and higher volumes as compared with other stabilized hyaluronan fillers may be applied (above 50 mL per application).

The most critical parameter influencing the in vivo performance of the hydrogel composition is the "degree of modification with thiol groups", which indicates the initial amount of thiol groups (typically given in μmol) per gram (g) of the thiol-modified hyaluronan and is abbreviated as DoM. This amount of thiol groups is a characteristic of the thiol-modified hyaluronan raw material and indicates the amount of thiol groups which are available for crosslinking during the production process of the composition. Thiol groups or moieties may also be referred to as mercapto or sulfhydryl groups. Based on various examples, the inventors identified an optimal range for the degree of modification between about 80 μmol per g polymer to about 280 μmol per g polymer. On the one hand, a degree of modification above 80 μmol per g polymer was necessary to produce compositions with a volumizing effect of more than 12 weeks after implantation. Surprisingly, on the other hand, using thiol-modified hyaluronan with higher degrees of modification did result in lower depot volume after 84 days (e.g. 350 μmol per g polymer as shown in Example 9, ID10). Thus, the initial degree of modification of the thiol-modified hyaluronan with thiol groups was identified as a crucial factor that—in interplay with the polymer concentration and the polymer molecular weight—influences the rheological and in vivo properties of a sterile hydrogel composition. The desired residence time after implantation into a soft tissue was only obtained with compositions comprising crosslinked thiol-modified hyaluronan with an initial degree of modification in a narrow range of from 80 to 280, preferably from 100 to 240, more preferably from 120 to 200 μmol thiol groups per g polymer.

Besides the degree of modification, parameters that remarkably influence the rheological and in vivo properties of the hydrogel are the concentration of the crosslinked thiol-modified hyaluronan as well as the molecular weight distribution of the hyaluronan chains.

It is preferred that the crosslinked polymer has a mean reduced post-sterilisation molecular weight of more than about 200 kDa, e.g. more than about 250 kDa, preferably more than about 300 kDa, more preferably more than about 350 kDa, wherein the mean reduced post-sterilisation molecular weight is defined as the mean molecular weight of a reduced thiol-modified hyaluronan from said sterile hydrogel composition after exposing said crosslinked polymer to reductive conditions. The "mean reduced post-sterilisation molecular weight" of the crosslinked polymer was identified as an additional critical factor influencing the residence time of the hydrogel after implantation and will be abbreviated as MRPMW in the following. The MRPMW is determined as the molecular weight of a crosslinked thiol-modified hyaluronan (crosslinked polymer) after a preparation step, wherein the crosslinked polymer of the hydrogel composition is exposed to reductive conditions. In the hydrogel, the crosslinked polymer represents a complex network, for which a molecular weight may not be determined. Thus, it is necessary to reduce the crosslinked polymer, i.e. the crosslinking disulfide bonds are cleaved prior to determining the molecular weight. The MRPMW is a value that relates to the mean molecular weight of the polymer chains of the crosslinked polymer in the hydrogel composition. The MRPMW is defined as mean molecular weight (MMW) of a reduced thiol-modified hyaluronan from the sterile hydrogel composition, i.e. the MMW for the fraction of thiol-modified hyaluronan as determined in or obtainable from the composition post-sterilisation and post-reduction. Usually, the MRPMW determined for a thiol-modified hyaluronan from the sterile hydrogel composition is lower when compared to the mean molecular weight (MMW) of the raw material, i.e. the thiol-modified hyaluronan, which is used for the production of the corresponding compositions (see Table 1). The reduction of the MRPMW in comparison to the MMW of the raw material is assumed to be the consequence of the hydrogel production procedure including sterilisation. Accordingly, using the MRPMW of the crosslinked polymer is more appropriate to characterize the hydrogel composition than using the MMW of the raw material.

However, the inventors found that when using a thiol-modified hyaluronan with a mean molecular weight (MMW) of at least about 400 kDa, preferably at least about 500 kDa, more preferably at least about 600 kDa, such as about 700 kDa, for the production of hydrogel compositions, the MRPMW of the crosslinked polymer in the hydrogel composition was about 250 kDa or higher. For example, the production procedures outlined in the examples starting with a thiol-modified hyaluronan of about 600 kDa resulted in hydrogel compositions with a MRPMW of the crosslinked polymer being in the most preferable region of about 350 kDa or higher. Vice versa, a MRPMW of about 200 or 250 kDa or higher is an evidence that the respective thiol-modified hyaluronan has a MMW being at least about 400 kDa, although the quantitative relation depends on the production procedure.

In a composition according to the invention, the MRPMW of the crosslinked polymer preferably is about 250 kDa or higher. Examples with compositions comprising a crosslinked polymer with a MRPMW below 100 kDa, e.g. 90 kDa, did not show an intradermal residence time over a sufficiently long time period, whereas an example composition comprising a crosslinked polymer with a MRPMW of about 410 kDa and an initial degree of modification with thiol groups in the same order of magnitude showed a mean relative depot volume above 50% for 170 days. According to the inventor's knowledge, the state of the art is silent about MRPMW and its role or the MMW of the thiol-modified hyaluronan for influencing in vivo performance of a hydrogel after implantation into a soft tissue.

The MRPMW is characterising the cross-linked polymer, i.e. a non-uniform network, in the hydrogel composition via a rather indirect measure. Thus, it is not surprising that the results typically show a deviation of ±10% or sometimes even higher. Example 5 specifies an exemplary method of determining the MRPMW. A person skilled in the art will acknowledge that other approaches may arrive to comparable values for this parameter. For example, agarose gel electrophoresis can be used to separate different MW fractions of hyaluronan in an agarose gel using a horizontal gel chamber and a hyaluronan molecular weight ladder as marker. Stained gels are then densitometrically analyzed followed by molecular mass calculation.

In another embodiment, the crosslinked thiol-modified hyaluronan preferably is comprised in the composition with a concentration of at most 14 mg/mL, preferably at most 13 mg/mL, i.e. by weight in respect to the volume of the sterile hydrogel composition. The concentration preferably refers to the concentration of the salt, e.g. the sodium salt of the crosslinked thiol-modified hyaluronan. Accordingly, an equivalent amount of thiol-modified hyaluronan is provided for the preparation of the hydrogel. Higher concentrations are not considered suitable as they result in hydrogel compositions with high elasticity and without acceptable injectability. Concentrations of 3 mg/mL or lower are not considered suitable due to low elastic modulus G' observed for such hydrogel compositions. Within the range of about 4 mg/mL to about 14 mg/mL, e.g. 5 or 9 or 12 mg/mL, good rheological properties were observed.

The invention also provides a method for producing a sterile hydrogel composition according to the invention comprising the steps of:

a) providing a thiol-modified hyaluronan, wherein the thiol-modified hyaluronan has a degree of modification with thiol groups of more than about 80 µmol per gram polymer, preferably more than about 105 µmol per gram polymer, more preferably more than about 120 µmol per gram polymer, wherein the thiol-modified hyaluronan has a degree of modification with thiol groups of less than about 280 µmol per gram polymer, preferably less than about 240 per gram polymer, more preferably less than 200 µmol per gram polymer, and wherein the thiol-modified hyaluronan has a mean molecular weight of at least 400 kDa, preferably at least 500 kDa, more preferably at least 600 kDa, in an aqueous solution, b) oxidizing the thiol-modified hyaluronan by exposing the previously obtained aqueous solution to conditions that allow the thiol-modified hyaluronan to form a disulfide crosslinked polymer, wherein or whereby the aqueous solution becomes a hydrogel, optionally c) adding an unmodified polymer selected from the group of biocompatible polysaccharides to the previously obtained hydrogel or to the previously obtained solution, optionally d) sieving the previously obtained hydrogel to obtain a hydrogel with a particular particle size distribution, e) filling the previously obtained hydrogel into a container, preferably a syringe, and exposing the filled container to conditions allowing for sterilization of the hydrogel, f) obtaining a sterile hydrogel composition in a container comprising a crosslinked polymer.

In the method for producing a sterile hydrogel the steps may be conducted in different sequences. Especially the steps of crosslinking (oxidizing), adding an unmodified polymer and sieving may be performed in different sequences without necessarily affecting the hydrogel quality. Preferably, the steps are conducted in the sequence a), c), b), d), e) and f), wherein the preparation of the solution (step a) and the addition of the unmodified polymer (step c) may be performed concomitantly and optionally a further component (e.g. a local anaesthetic agent) may be added at the same time.

In another aspect, the invention provides the composition according to the invention for use as medicine, in particular for use in the treatment and prevention of soft tissue conditions. Furthermore, the invention relates to the cosmetic use of the composition according to the invention. Such uses (therapeutic or cosmetic) may be referred to the use of the composition according to the invention as soft tissue filler or for tissue augmentation. Such uses preferably include the application, e.g. by injection or implantation, to a human being, while the applicability is not limited to the human species.

In another aspect, the invention relates to a method, wherein the method comprises introducing the composition according to the invention, preferably by injection from a syringe, at a specific soft tissue site. The method relates to the use of the composition as soft tissue filler or for fine line treatment for therapeutic as well as cosmetic purposes.

In one embodiment, uses or methods according to these aspects comprise that the hydrogel composition is introduced into a tissue site by injection from a syringe intradermally, supraperiosteally or subcutaneously into a human being.

Moreover, the invention provides an application unit for injection comprising a syringe and at least one hypodermic needle, wherein the syringe is filled with a hydrogel composition according to the invention.

SHORT DESCRIPTION OF THE FIGURES

DETAILED DESCRIPTION OF THE INVENTION

Figure 1:
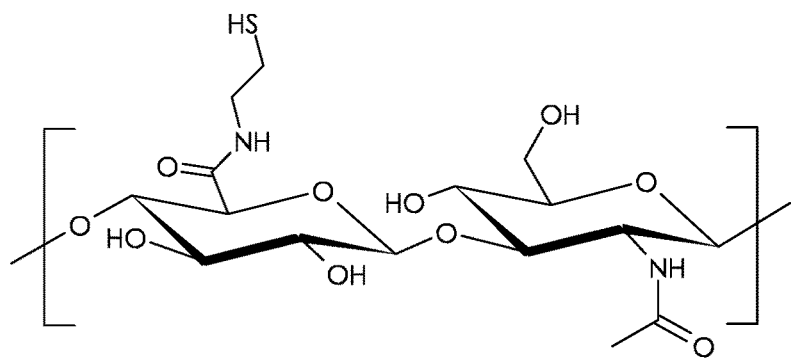
FIG. 1 shows a schematic presentation of a hyaluronan-cysteamine substructure.

The properties of the sterile hydrogel according to the invention are critically influenced by the thiol-modified hyaluronan, especially its degree of modification. Established methods for determining the degree of modification include the Ellman method or measuring the release of a chromophoric thione upon reaction of 2,2'-dithiodipyridine with thiol-bearing agent (see Example 1). Those skilled in the art will also know alternative methods resulting in similar values. Herein, the degree of modification is given in µmol of thiol groups per gram polymer. Alternatively, the degree of modification may be indicated as percentage, wherein the amount of modified repeating units is divided by the total amount of HA-repeating units in the polymer (D-glucuronic acid and N-acetyl-D-glucosamine). The degree of modification in µmol of thiol groups per gram polymer can be converted in percentage by taking into account the molecular weight of 400 g/mol of the HA-repeating unit. In this conversion, the change of molecular weight introduced by the modification is typically neglected. Accordingly, the degree of modification as specified for the thiol-modified hyaluronan in a composition according to the invention may be expressed as ranging between 3.2% and 12.0%, preferably between 4.0% and 11.2% or 4.8% and 10%.

The "thiol-modified hyaluronan" (HA-SH) is a thiol-group containing derivative of a hyaluronic acid (HA). It is characterised by the degree of modification as specified above and is accessible via known synthetic approaches starting from hyaluronan which is available in different molecular weights (or molecular weight ranges). Numerous examples of HA modification with thiol group bearing ligands can be found in scientific and patent literature: Griesser et al. provides a review of thiolated hyaluronic acid polymers (Griesser et al., Polymers 10 (2018) 243). Aeschlimann (EP 1 115 433 B1) describes a method of functionalization of HA which does not compromise the molecular weight of HA and which further provides HA molecules that are well tolerated in vivo and are biodegradable. The method is used to generate HA with different terminal functional groups for crosslinking, such as thiol groups. These side chains are introduced into HA by carbodiimide-mediated coupling of primary (protected) thiol group containing amines or disulfide-bond containing diamino or dihydrazide ligands to the carboxyl group of the glucuronic acid moiety using an active ester intermediate. Intermediate products with disulfide bonds are then reduced and intermediate products with protected thiol groups are then deprotected by removing the protecting group. Another method is described by Bulpitt et al. (U.S. Pat. No. 6,884,788) which comprises a direct reaction of the HA carboxyl group with a disulfide-bond containing carbodiimide (such as 2,2'-dithiobis(N-ethyl-(N'-ethylcarbodiimide), followed by reducing the disulfide bond with a reducing agent. WO 2008/008857 A2 discloses synthesis methods for 2-thioethyl ether derived hyaluronan. EP 0 587 715 discloses how to synthesize water insoluble anionic polysaccharides via dissolving at least one polyanionic polysaccharide (e.g., HA), in an aqueous mixture; activating the polyanionic polysaccharide with an activating agent such as a diimide, e.g. EDC or ETC, or BOP; modifying the activated polyanionic polysaccharide with a modifying compound such as 1-hydroxy-benzotriazole hydrate (HOBt) or 1-hydroxy-benzotriazole monohydrate; and reacting the activated polyanionic polysaccharide with a suitable nucleophile (such as an amino thiol) to form the desired insoluble composition. The inventors state that one major advantage of the BOP activation of polyanionic polysaccharide is that the molecular weight of the polyanionic polysaccharide is not decreased upon coupling to the nucleophile. EP 1 790 665 B1 describes a water-soluble modified hyaluronic acid, which is produced by introducing a substituent into the carboxy group of the glucuronic acid of hyaluronic acid, via an amide bond using a BOP condensing agent in an aprotic polar solvent. Diamines with a disulfide bond are among the listed substituents. Triazine-mediated amidation with DMT-MM for efficient and controlled functionalization of hyaluronic acid with cysteamine is described in Borke et al., wherein the mild reaction conditions and the minimal degradation of the polysaccharide chain are listed as advantages of using this group of coupling agents in comparison to other coupling reagents such as EDC-mediated substitution (Borke et al., Carbohydrate Polymers 116 (2015) 42-50). Liang et al. describe the introduction of thiol groups to HA via an amidation reaction of the side carboxylates with cystamine in the presence of CDMT and NMM, followed by a reducing reaction with DTT (Liang et al. Carbohydrate Polymers 132 (2015) 472-480). The thiol modification of HA with 1-cysteine ethyl ester hydrochloride by means of the double catalytic system-carbodiimide/Nhydroxysuccinimide was described in Kafedjiiski et al. (Int J Pharm 343, 48-58; 2007). In WO 2004/037164 hyaluronan was modified with 3,3'-dithiobis (propanoic dihydrazide) (DTP) or 4,4'-dithiobis(butyric dihydrazide) (DTB). After reduction with a reducing agent such as DTT the corresponding thiolated HA derivatives HA-DTPH and HA-DTBH were obtained. EP 2 103 631 also describes introduction of a thiol group bearing ligand via the carboxylic groups of HA by a hydrazide coupling method. Different thiolated HA polymers (HA-DGDTPDH, HA-DPDTPDH, HA-DSCDH) were synthesized.

According to the present invention, the thiol-modified hyaluronan preferably is a conjugate of a modification agent linked to hyaluronan.

Introduction of the modification agent via formation of an ester bond, amide bond or hydrazide bond between the carboxyl group of the glucuronic acid moiety of hyaluronan and the modification agent is preferred. The modification agent may comprise thiol groups in the form of disulfide bonds or as protected thiol groups during the synthesis process.

In one preferred embodiment, the modification agent is linked to the carboxyl group of the glucuronic acid moiety in the hyaluronan via an amide bond. Accordingly, the modification agent comprises at least one amino group capable to form the amide bond with the carboxyl group of the glucuronic acid moiety in the hyaluronan and the modification agent comprises a thiol group. For example, the thiol-modified hyaluronan is a hyaluronan-cysteamine conjugate, wherein cysteamine is linked to hyaluronan via an amide bond (see FIG. 1).

Similarly, other thiol group bearing modification agents may be used for the synthesis of thiol-modified hyaluronan via amide bond formation between an amino group (primary or secondary amino group, preferably primary amino group) of the modification agent and the carboxyl group of the glucuronic acid moiety in the hyaluronan.

A hyaluronan-homocysteine conjugate (FIG. 2 A) was synthesized by amidation of sodium hyaluronate with homocysteine thiolactone, exploiting its unique thiol protection as thiolacton. Free thiol groups were subsequently successfully liberated by alkaline hydrolysis in presence of a reducing agent to avoid unwanted gelling caused by disulfide formation.

Further modification agents include for example derivatives of cysteamine, cysteine or homocysteine, wherein the N-terminus of the cysteamine, cysteine or homocysteine is coupled with the carboxyl group of an amino acid. These derivatives are preferably synthesized by amidation of N-protected amino acids with cysteamine, cysteine or homocysteine, using routine peptide coupling reagents, preferably those enabling facile product purification, e.g. through removal of reactants and side products by an aqueous extraction upon reaction work up (see example 14 A for synthesis of thiol group bearing modification agents). Alternatively, cysteamine, cysteine or homocysteine are reacted with corresponding active esters of N-protected amino acids in organic solvents, such as succinimidyl esters. A hyaluronan-glycyl-cysteamine conjugate (FIG. 2 B) is an example for the thiol-modified hyaluronansynthesized by this approach.

A low molecular weight of the modification agent is preferred to conserve to the unique physico-chemical properties of hyaluronan as much as possible. Suitable low molecular weight modification agents to obtain a crosslinkable thiol-modified hyaluronan useful for a composition according to the invention preferably are further selected from the group comprising glutathione, cysteine, aminoalkylthiols comprising a linear or branched $C_2$-$C_6$-alkyl chain, homocysteine, carboxylate esters of homocysteine (e.g. $C_2$-$C_6$-alkyl esters of homocysteine, preferably ethyl homocysteine), and carboxylate esters of cysteine (e.g. $C_2$-$C_6$-alkyl esters of cysteine, preferably ethyl cysteine).

Aminoalkylthiol linkers can be conveniently introduced via corresponding symmetrical diamines, containing a disulfide linkage as a kind of inherent protecting group, exploited upon amide synthesis with hyaluronan. The disulfides can in turn be accessed starting from N-protected aminoalcohols: After introducing a thioester moiety, for example following Mitsunobu's protocol, saponification of the thioester under oxidative conditions delivers the desired target compounds (e.g. Example 14 C). An N-mercapto-n-butylhyaluronamide (FIG. 2 C) is an example for the thiol-modified hyaluronan synthesized by this approach (Example 15).

In another preferred embodiment, the modification agent is linked to the carboxyl group of the glucuronic acid moiety in the hyaluronan via a hydrazide bond. Accordingly, the modification agent comprises at least one hydrazide group capable to form the amide bond with the carboxyl group of the glucuronic acid moiety in the hyaluronan and the modification agent comprises a thiol group. For example, the thiol-modified hyaluronan is a hyaluronan-3-mercapto-propionic acid hydrazide conjugate (HA-DTPH) or a hyaluronan-2-mercapto-ethyl-carbonyl-amino-acetic acid hydrazide conjugate (HA-DGDTPDH; see Example 14 B, FIG. 2 D).

Formation of disulfide bonds (crosslinking) naturally occurs at physiological pH values in the presence of oxygen (e.g. supplied via the surrounding air or dissolved in an aqueous solution). The addition of a further oxidizing agent might be beneficial to accelerate disulfide formation. Suitable and well established oxidizing agents are for example hydrogen peroxide (or other peroxides), ascorbic acid, dimethyl sulfoxide and hypochlorous acid (sodium hypochlorite). Under excess pressure conditions pure oxygen gas or a high oxygen gas mixture can be used to increase the concentration of oxygen, which is then available as oxidation agent in the polymer aqueous solution.

Crosslinking of the thiol-modified hyaluronan (i.e. the formation of disulfide bonds) should be mostly complete before the hydrogel is further processed (i.e., undergoing further processing steps such as sieving, homogenization, filling into syringes and sterilization) in order to produce hydrogels with reproducible and stable characteristics such as the rheological properties. However, a certain small amount of thiol groups might not be available for disulfide formation due to factors like sterical hindrance. The fraction of non-crosslinked thiol groups in the crosslinked polymer may be determined via the residual thiol content expressed in µmol per g polymer. A high degree of crosslinking (via oxidation of the thiol groups) is regarded as beneficial for obtaining hydrogels with elastic properties suitable for a soft tissue filler.

Accordingly, in a preferred embodiment, the hydrogel composition according to the invention has a residual thiol content of less than 20%, preferably less than 15% in respect to the degree of modification of the thiol-modified hyaluronan. This corresponds to more than 80%, preferably more than 85% of the thiol groups of the thiol-modified hyaluronan being oxidized during the hydrogel production process.

The term "sterile" as used herein is to be understood in accordance with the art specifying a composition complying with the microbiological standards as defined for cosmetic or pharmaceutical products, for example in the United States Pharmacopoeia (USP), the European Pharmacopoeia (Ph. Eur.) or other national standards. Classically, the hyaluronan gels are sterilized after being filled into syringes. Thermal moist-heat sterilization with an autoclave is one of the standard methods, which comprises subjecting the HA gels to high-pressure saturated steam at 121° C. for around 15-20 minutes. Autoclaving for shorter time periods (for example, between about 1 minute and 5 minutes) and at higher temperatures (for example, between about 130° C. and 135° C.) might lead to a better preservation of the molecular weight of the HA molecules in the gels (see M. L. Bernuzzi, A. Giori, "An innovative way to thermally sterilize hyaluronic acid pre-filled syringes", 2016 white paper available under fedegari.com/wp-content/uploads/2019/03/WP-Fedegari-Thermal-sterilization-PFS-with-Hyaluronic-Acidv-2.pdf, US 2016/0220729). The optimization of other autoclaving parameters (such as ensuring rapid cooling of the product) might be additionally advantageous for preserving the molecular weight of the polymer (steriflow.com/en/news/Sterilization-hyaluronic-acid).

The term "hydrogel" as used herein is to be understood as describing a composition, which has both solid and fluid (liquid) characteristics. On one hand, the hydrogel may be injectable, i.e. it shows a fluid-like behavior. On the other hand, the hydrogel may be stiff (or rigid) enough to maintain a certain form, e.g. the hydrogel may be provided in the form of a preformed implant, thread or a filament. Thus, the term hydrogel alone does not limiting the rheological properties of the composition in a quantitative manner.

However, in one embodiment, the hydrogel has an elastic modulus G' of at least 50 Pa (50,000 mPa) measured at 25° C. using a rheometer with a shear rate of 1 Hz. The hydrogel's elastic modulus G' is directly influenced by the factors
- degree of crosslinking (being defined by the critical degree of modification, i.e. a characteristic according to the present invention),
- the concentration of the crosslinked polymer, and the MRPMW (being dependent on the mean molecular weight of the thiol-modified hyaluronan).

Hydrogels with an elastic modulus G' of at least 1,000 Pa showed a volumizing effect and long term residence time. On the other hand, lower elastic moduli G' may be preferred for the application as smooth filler. The examples show that a long residence is also achieved with hydrogel compositions ID5 and ID6, having a G' of about 90 Pa or 400 Pa. Thus, the hydrogel according to the invention may have an elastic modulus G' of at least 80 Pa or at least 350 Pa, or even at least 600 Pa. And, in some embodiments, the elastic modulus G' of the hydrogel is at most 1,600 Pa, preferably at most 1,000 Pa, more preferably at most 900 Pa.

In a preferred embodiment, the extrusion force for an injectable hydrogel composition according to the present invention is preferably less than 30 N, as measured with a 30 G needle at an extrusion rate of 12 mm/min using a standard 1 mL glass syringe.

In another preferred embodiment, the composition further comprises an unmodified polymer selected from the group of biocompatible polysaccharides. Preferably, the unmodified polysaccharide is unmodified hyaluronan (HA). The unmodified (non-crosslinked) or also referred to as free hyaluronan can complement the hydrogel composition. Unmodified HA is commonly added as a lubricant to soft tissue fillers to ensure easy injectability by decreasing the extrusion force required to inject the products through a needle or cannula. Preferably, the free hyaluronan raw material used for the production of the composition has a molecular weight in the range of about 500 kDa to about 3,500 kDa. However, due to the fast degradation of unstabilized hyaluronan, the person skilled in the art will understand that the in vivo performance of the composition as soft tissue filler is largely driven by the crosslinked polymer and the properties of the underlying thiol-modified hyaluronan. The fraction of unmodified polysaccharide in the total polymer content of the composition is preferably less than ⅔. It is preferred that the unmodified polysaccharide is comprised in a concentration equal or lower than the crosslinked polymer. Exemplarily, an unmodified hyaluronan is comprised in the compositions at concentrations of 3 mg/mL to 9 mg/mL, such as 5 or 7 mg/mL, wherein the concentration preferably refers to the concentration of a salt, e.g. sodium hyaluronate.

The hydrogel composition may include a local anaesthetic agent and/or one or more components selected from a variety of other components, such as, growth factors, vitamins, polyalcohols, alkali metal halides, minerals, antioxidants, amino acids, coenzymes, ceramic particles (such as calcium hydroxyl apatite particles), polymeric particles, polymers (such as polyethylene glycol, glycosaminoglycans, lubricins, polysaccharides, and their derivatives), proteins (such as elastin, collagen, keratin, silk fibroin), anticellulite agents, anti-scarring agents, anti-inflammatory agents, anti-irritant agents, vasoconstrictors, anti-hemorrhagic agents (such as hemostatic agents and anti-fibrinolytic agents), tensioning agents, anti-acne agents, pigmentation agents, anti-pigmentation agents, anti-phlogistic agents, anti-rheumatic agents, anti-viral agents, anti-infective agents, anti-septic agents, chemotherapeutic agents, cytostatic agents, anti-allergic agents, anti-varicosic agents, analgesics, antibiotics, antimycotics, spasmolytics, antihistamines, agents for treating hemorrhoids, therapeutic agents for treating the skin, and moisturizing agents.

The addition of a local anaesthetic agent to the hydrogel composition is particularly desirable in view of its ability to mitigate pain upon injection. Preferably, the anaesthetic agent is lidocaine, such as in the form of an acid addition salt, e.g. lidocaine HCl.

In a method for producing the hydrogel a local anaesthetic agent and/or one or more components may be added during different production steps, i.e. in one embodiment the local anesthetic agent and/or one or more components is/are added during optional step c) or in another embodiment independently from adding the unmodified polymer e.g. added to the solution during step a) or to the hydrogel obtained in step c) or d). In a preferred embodiment, an anaesthetic agent, e.g. lidocaine HCl, is added during step a) or during step c). In an embodiment, wherein step c) precedes step b), i.e. wherein an unmodified hyaluronan is added prior to crosslinking, it is preferred that also a local anaesthetic agent and/or one or more further components are included prior to the crosslinking step.

Furthermore, it will be understood that a main component of the hydrogel composition is water. Preferably, water for injection or purified water is used for producing the composition. Besides, it will be acknowledged that the composition may be buffered to exhibit a physiologically acceptable pH in the range of 6.7 to 7.8. Suitable buffers are known to those skilled in the art and include for example phosphate buffer. The composition also exhibits a physiologically-acceptable osmolality, which is similar to the normal osmolality of extracellular fluid in the subject to be treated (e.g. in humans). Thus, the composition may have an osmolality in the range of 250-350 mOsm/kg and may include additional solutes to adjust the osmolality, such as sodium chloride, calcium chloride, and/or potassium chloride.

Soft tissue fillers comprising biomaterials such as stabilized hyaluronan are delivered to the tissue site, where augmentation is desired by means of an injectable hydrogel composition. The aims of the uses or methods referring to soft tissue filling include to augment soft (dermal) tissue, to correct congenital anomalies, acquired defects or cosmetic defects.

The main effect of the hydrogel composition is purely physical as it has a filling effect based on the original volume and the swelling of the implant. Thus, in absence of any physiological or pharmacological interaction, the use may be classified as cosmetic and the composition may be considered as a cosmetic or medical device. Applications, wherein the use of the hydrogel composition according to the invention may be considered as cosmetic include for example the reduction of signs of age, e.g.

application into the tissue of the vulva and vagina for nonsurgical female genital rejuvenation purposes application into the dermis, subdermal or supraperiosteal application.

Exemplarily, the hydrogel composition may be used (in a method) for cosmetic purposes, e.g. for filling wrinkles, for treating skin defects, for restoring lost volume of the face or the body (e.g. breast, ear lobe), for reducing dimples in cellulitis, for treating tear trough deformities, for shaping the contours of the face or the body (e.g. buttock enhancement, hip augmentation, calf augmentation), for penis enlargement (penile girth enhancement, glans penis augmentation).

In other cases the filling and augmentation of a soft tissue may result in a treatment or prevention of a disease, i.e. wherein symptoms of the disease are reduced, alleviated and/or prevented from (re-)occurrence. Disease that are caused by a soft tissue defect may benefit from the temporary and/or local structural filling, damping, support or augmentation of the surrounding tissue by the applied hydrogel. Diseases, wherein the hydrogel composition may be used for treatment or prevention include for example
- metatarsalgia, a pain disease of the fatty pad of the ball of the foot, for which use the hydrogel according to the invention may be applied at the fatty pad of the ball of the foot soft tissue,
- urinary or fecal incontinence, for which indications the hydrogel according to the invention may be applied at the tissue defining sphincters,
- vulvovaginal atrophy (also genito-urinary syndrome of menopause), for which indication the hydrogel according to the invention may be applied at the vulvovaginal area via injection into the vaginal mucosa and the vestibule and/or for labia majora augmentation, wherein a reconstruction of the labia majora will ensure a close contact between both labia majora to protect the inner structures of the vulva
- vocal cord impairment,
- venous valve insufficiency, or
- facial lipoatrophy, debilitating scars or morphological asymmetry or deformation (congenital or resulting as consequence of trauma or surgery, e.g. of the thorax or of the face), for which indications the hydrogel is applied for reconstructive purposes.

As to the application unit including a syringe filled with the hydrogel composition according to the invention, it is preferred that the unit includes an instruction to use, e.g. describing the cosmetic or medical application(s). The hypodermic needle preferably has lumen measured in Gauge (G) of at least 27 G, preferably of from 27 G to 32 G. In one embodiment, the application unit comprises at least two hypodermic needles, which differ from each other in their lumen. The latter allows the provision of a kit, wherein the user, e.g. medical staff, can choose between different needles depending on the intended application. In this embodiment, preferably the instruction to use describes the suitability of different needles for different cosmetic or medical applications (e.g. different injection sites).

EXAMPLES

Example 1—Determination of Degree of Modification

Quantification of thiol groups in a thiol-modified hyaluronan (HA-SH) used as raw material for preparation of hydrogel compositions is based on a wet chemistry method employing 2,2'-dithiodipyridine (DTDP). Free thiol moieties which are covalently bound to a polymeric backbone undergo thiol-disulfide exchange reaction with DTDP, whereas one equivalent of a chromophoric thione is released. In buffered acidic medium (pH=4), the absorption of the resulting thione can be measured photometrically at 343 nm.

About 420 mg of thiol-modified hyaluronan were accurately weighed and dissolved in 30 g of 0.01 N HCl under continuous magnetic stirring for 2-3 hours to prepare a stock solution. Then, about 310 mg of the stock solution were accurately weighed and mixed with 4200 mg acetate buffer pH 4 in an eppendorf tube to prepare a sample solution. Three sample solutions were prepared from each stock solution. 25.0 mg N-acetylcysteine were accurately weighed and solved in 25.0 mL of acetate buffer (pH 4). This solution was then further diluted with acetate buffer (pH 4) for the preparation of a calibration curve. Acetate puffer was used for the blank value. 500 μL of a solution containing 0.125 mg/mL of DTDP in acetate buffer (pH 4) were added to 500 μL of each sample solution (calibration curve, sample solution and blank value). The solutions were briefly homogenized and incubated for 30 min at room temperature. Finally, each sample (calibration curve, sample solution and blank value) was transferred into a microcuvette and measured at 342 nm in a spectrophotometer against the blank value.

Example 2—Determination of Residual Thiol Content

For the determination of the residual thiol content of the crosslinked polymer in the hydrogel composition (i.e. the HA-SH polymer after crosslinking and production of the compositions) a similar method as described above was used.

About 50 mg of each sample hydrogel were accurately weighed and mixed with 1.3 mL of a solution containing 0.125 mg/mL of DTDP in acetate buffer (pH 4). 25.0 mg N-acetylcysteine were accurately weighed and solved in 200.0 mL of acetate buffer (pH 4). This solution was then further diluted with acetate buffer (pH 4) for the preparation of a calibration curve. Acetate puffer was used for the blank value. 500 μL of a solution containing 0.125 mg/mL of DTDP in acetate buffer (pH 4) were added to 500 μL of each sample of the calibration curve and the blank. All samples were incubated under continuous agitation for 120 min at room temperature. After centrifugation of all samples 500 μL of each supernatant were further diluted with 500 μL acetate buffer and measured at 342 nm in a spectrophotometer against the blank value.

Example 3—Methods of Producing a Hydrogel Composition

Method A
Dissolution: thiol-modified hyaluronan, unmodified hyaluronan, and lidocaine HCl are concomitantly dissolved in an aqueous solution
Crosslinking: After adjustment of the pH to about 6.8 to 7.6 thiol-modified hyaluronan is crosslinked via the oxidation of thiol groups to disulfide bridges by oxygen
Sieving: Optionally the hydrogel comprising crosslinked thiol-modified hyaluronan, unmodified hyaluronan and lidocaine HCl is pressed through a filter plate with a defined mesh size (once or multiple times)
Sterilization: Autoclavation after filling of the hydrogel into syringes
Method B
Dissolution: Thiol-modified hyaluronan, unmodified hyaluronan, and lidocaine HCl are concomitantly dissolved in an acidic aqueous solution.
Crosslinking: After adjustment of the pH to about 6.8 to 7.6 thiol-modified hyaluronan is crosslinked via the oxidation of thiol groups to disulfide bridges by an oxidation agent and oxygen.
Sieving: Optionally the hydrogel comprising crosslinked thiol-modified hyaluronan, unmodified hyaluronan and lidocaine HCl is pressed through a filter plate with a defined mesh size (once or multiple times).
Sterilization: Autoclavation after filling of the hydrogel into syringes
Method C
Dissolution: Thiol-modified hyaluronan is dissolved in an aqueous solution; a separate solution comprising unmodified hyaluronan and lidocaine HCl in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by oxygen.

Sieving: The hydrogel comprising crosslinked thiol-modified hyaluronan is pressed through a filter plate with a defined mesh size (once or multiple times).

Homogenization: The hydrogel comprising crosslinked thiol-modified hyaluronan and the solution comprising unmodified hyaluronan and lidocaine HCl are homogenized and optionally pressed through a filter plate with a defined mesh size (once or multiple times).

Sterilization: Autoclavation after filling of the hydrogel into syringes

Method D

Dissolution: Thiol-modified hyaluronan is dissolved in an aqueous solution; a separate solution comprising unmodified hyaluronan and) lidocaine HCl in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by an oxidation agent and oxygen.

Sieving: The hydrogel comprising crosslinked thiol-modified hyaluronan is pressed through a filter plate with a defined mesh size (once or multiple times).

Homogenization: The hydrogel comprising crosslinked thiol-modified hyaluronan and the solution comprising unmodified hyaluronan and lidocaine HCl are homogenized and optionally pressed through a filter plate with a defined mesh size (once or multiple times).

Sterilization: Autoclavation after filling of the hydrogel into syringes

Method E

Dissolution: Thiol-modified hyaluronan and lidocaine HCl are dissolved in an aqueous solution; a separate solution comprising unmodified hyaluronan in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by oxygen.

Sieving: The hydrogel comprising crosslinked thiol-modified hyaluronan and lidocaine HCl is pressed through a filter plate with a defined mesh size (once or multiple times).

Homogenization: The hydrogel comprising crosslinked thiol-modified hyaluronan and lidocaine HCl and the solution comprising unmodified hyaluronan are homogenized and optionally pressed through a filter plate with a defined mesh size (once or multiple times).

Sterilization: Autoclavation after filling of the hydrogel into syringes.

Method F

Dissolution: Thiol-modified hyaluronan and lidocaine HCl are dissolved in an acidic aqueous solution; a separate solution comprising unmodified hyaluronan in phosphate buffer (pH 6.8-7.6) is prepared.

Crosslinking: After adjustment of the pH to about 6.8 to 7.6 thiol-modified hyaluronan is crosslinked via the oxidation of thiol groups to disulfide bridges by an oxidation agent and oxygen.

Sieving: The hydrogel comprising crosslinked thiol-modified hyaluronan and lidocaine HCl is pressed through a filter plate with a defined mesh size (once or multiple times).

Homogenization: The hydrogel comprising crosslinked thiol-modified hyaluronan and lidocaine HCl and the solution comprising unmodified hyaluronan are homogenized and optionally pressed through a filter plate with a defined mesh size (once or multiple times).

Sterilization: Autoclavation after filling of the hydrogel into syringes.

Method G

Dissolution: Thiol-modified hyaluronan, unmodified hyaluronan, and lidocaine HCl are consecutively dissolved in an aqueous solution.

Crosslinking: After adjustment of the pH to about 6.8 to 7.6 thiol-modified hyaluronan is crosslinked via the oxidation of thiol groups to disulfide bridges by oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method H

Dissolution: Thiol-modified hyaluronan, unmodified hyaluronan, and lidocaine HCl are consecutively dissolved in an acidic aqueous solution.

Crosslinking: After adjustment of the pH to about 6.8 to 7.6 thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method I

Dissolution solution 1: Thiol-modified hyaluronan, unmodified hyaluronan and lidocaine HCl are concomitantly dissolved in water.

Crosslinking solution 1: After adjustment of the pH to about 6.8 to 7.6 thiol-modified hyaluronan is crosslinked via the oxidation of thiol groups to disulfide bridges by an oxidation agent and oxygen.

Dissolution solution 2: Thiol-modified hyaluronan, unmodified hyaluronan and optionally lidocaine HCl are concomitantly dissolved in water.

Crosslinking: The pH of solution 2 is adjusted to about 6.8 to 7.6, immediately followed by mixing equal parts of the crosslinked solution 1 with solution 2. Thiol-modified hyaluronan is crosslinked via the oxidation of thiol groups to disulfide bridges by an oxidation agent and oxygen.

Sieving: Optionally the hydrogel comprising crosslinked thiol-modified hyaluronan, unmodified hyaluronan and lidocaine HCl is pressed through a filter plate with a defined mesh size (once or multiple times).

Sterilization: Autoclavation after filling of the hydrogel into syringes.

Method J

Dissolution: Thiol-modified hyaluronan and unmodified hyaluronan are dissolved in an aqueous solution; a separate solution comprising lidocaine HCl is prepared.

Crosslinking: After adjustment of the pH to about 6.7 to 7.8 thiol-modified hyaluronan is crosslinked via the oxidation of thiol groups to disulfide bridges by oxygen.

Sieving: The hydrogel comprising crosslinked thiol-modified hyaluronan and unmodified hyaluronan is pressed through a filter plate with a defined mesh size (once or multiple times).

Homogenization: The hydrogel comprising crosslinked thiol-modified hyaluronan and unmodified hyaluronan and the solution comprising lidocaine HCl are homogenized and optionally pressed through a filter plate with a defined mesh size (once or multiple times).

Sterilization: Autoclavation after filling of the hydrogel into syringes.

Method K

Dissolution: Thiol-modified hyaluronan and unmodified hyaluronan are dissolved in an aqueous solution; a separate solution comprising lidocaine HCl is prepared.

Crosslinking: After adjustment of the pH to about 6.7 to 7.8 thiol-modified hyaluronan is crosslinked via the oxidation of thiol groups to disulfide bridges by an oxidation agent and oxygen.

Sieving: The hydrogel comprising crosslinked thiol-modified hyaluronan and unmodified hyaluronan is pressed through a filter plate with a defined mesh size (once or multiple times).

Homogenization: The hydrogel comprising crosslinked thiol-modified hyaluronan and unmodified hyaluronan and the solution comprising lidocaine HCl are homogenized and optionally pressed through a filter plate with a defined mesh size (once or multiple times).

Sterilization: Autoclavation after filling of the hydrogel into syringes.

Example 4—Determination of Elastic Modulus G'

Oscillatory rheological measurements of all compositions were performed using an Anton Paar MCR 102 Rheometer with a cone-plate system. The compositions were transferred to the rheometer via injection through a 27 G needle (or without needle, where indicated). The elastic modulus was obtained during a frequency test with constant deformation within the linear viscoelastic region of the hydrogel at a temperature of 25° C. and a frequency of 1 Hz.

Example 5—Determination of Molecular Weight

A Viscotek TDAmax temperature controlled, multi-detector SEC system comprising high sensitivity detectors in series—Photodiode Array UV, Light Scattering (both RALS and LALS), Refractive Index and Viscometer was used for the measurements. The refractive index detector recorded the concentration of the sample resulting in the respective distribution curve. In combination with the light scattering detectors, the molecular weight (MW) was determined. For size exclusion chromatography (SEC) analysis, samples were diluted with PBS resulting in a final polymer concentration of 0.1 mg/mL.

Errors or fluctuations which occur during this test typically result in a deviation of about 10%.

Samples for determination of the mean reduced post-sterilisation molecular weight (MRPMW) were prepared by dispersing about 200 mg of the sterile investigated hydrogel composition in 1.8 mL phosphate buffered saline (PBS) and incubation for 2 hours at room temperature. Crosslinked thiol-modified hyaluronan was separated from free hyaluronan via centrifugation. The residue was redispersed in PBS. After repetitive extraction/centrifugation steps, the residual gel was treated with a reducing agent (TCEP·HCl (tris(2-carboxyethyl)phosphine hydrochloride)) for 3 hours to cleave disulfide bridges followed by the acidification of the resulting solution with 5 N HCl (reduction). The reduced thiol-modified hyaluronan was precipitated with ethanol and recovered by centrifugation (a thiol-modified hyaluronan from the sterile hydrogel composition). The precipitate was dissolved in 4 mL of an aqueous solution containing a capping agent for free thiol moieties (2-(2-aminoethyldisulfanyl)pyridine-3-carboxylic acid) in a concentration of 2 mg/mL. After 3 h incubation at room temperature the sample was further diluted with PBS.

Alternatively, the MRPMW of the crosslinked polymer was determined by a subtraction method. Both approaches result in similar values. After sterilization of a hydrogel composition comprising crosslinked polymer and free hyaluronan a reducing agent was added to the hydrogel to quantitatively break disulfide bonds. The MW distribution of thiol-modified hyaluronan in its reduced form and free hyaluronan was then determined simultaneously ($M_W$(total)). In addition, the MW of free hyaluronan was determined: 200 mg of the sterile investigated hydrogel composition were dispersed in 1.8 mL phosphate buffered saline (PBS) and incubated for 2 hours at room temperature. After centrifugation the supernatant was used for SEC analysis of the MW of free hyaluronan ($M_W$(HA)).

By determining the molecular weight of the free hyaluronan ($M_W$(HA)) and the combined molecular weight of the free hyaluronan and reduced thiol-modified hyaluronan ($M_W$(total)), the MRPMW (here $M_W$(HA-SH)) can be calculated according to equation (I), wherein $C_{HA}$ and $C_{HA-SH}$ represent the fraction of free hyaluronan and reduced thiol-modified hyaluronan, respectively:

$$M_W(HA-SH) = \frac{M_W(\text{total}) - M_W(HA)\frac{C_{HA}}{C_{HA}+C_{HA-SH}}}{\frac{C_{HA-SH}}{C_{HA}+C_{HA-SH}}} \quad (I)$$

Comparative results are given in Table 1 with the corresponding mean molecular weight (MMW) of the HA-SH raw material used for hydrogel production. Typically, the MRPMW is lower than the MMW. The production of the hydrogel composition influences the molecular weight distribution.

Example 6—Measurement of Extrusion Force

A 30 G needle was attached to a 1 mL syringe containing the hydrogel composition. The extrusion force was measured with a Mecmesin force testing system and an extrusion rate of 12 mm/min. Measurements were performed at least in triplicate. The calculated mean extrusion force (EF) for each tested hydrogel composition is listed in Table 1 and other hydrogel compositions.

Example 7—Sterile Hydrogel Compositions

Various compositions and their characteristics are listed in Table 1, wherein the main difference between the compositions lies in the concentration and the characteristics of the crosslinked polymer, which is an oxidation product of HA-cysteamine. Sterile hydrogel compositions comprising crosslinked HA-cysteamine, unmodified sodium hyaluronate and 3 mg/mL lidocaine HCl were produced with similar methods (compare methods A, B and I above).

Hydrogel compositions ID 1 to ID 4 were produced with a hyaluronan-cysteamine polymer with a MMW of 150 kDa and a degree of modification of 118 μmol/g. Hydrogel compositions ID 1 to ID 3 comprised 3 mg/mL unmodified sodium hyaluronate and 6 mg/mL (ID 1), 9 mg/mL (ID 2) and 13 mg/mL (ID3) crosslinked hyaluronan-cysteamine, respectively. Hydrogel composition ID 4 comprised 4 mg/mL unmodified sodium hyaluronate and 13 mg/mL crosslinked hyaluronan-cysteamine.

Hydrogel compositions ID 5 and ID 6 were produced with a hyaluronan-cysteamine polymer with a MMW of 730 kDa and a degree of modification of 151 µmol/g. Hydrogels ID 5 and ID 6 comprised 3 mg/mL unmodified sodium hyaluronate (MMW 2.41 MDa) and 5 mg/mL (ID 5) and 9 mg/mL (ID 6) crosslinked hyaluronan-cysteamine sodium salt, respectively.

Hydrogel compositions ID 7 and ID 8 were produced with a hyaluronan-cysteamine polymer with a MMW of 780 KDa and a degree of modification of 149 µmol/g. Hydrogel composition ID 7 comprised 3 mg/ml unmodified sodium hyaluronate (MMW 1.94 MDa), and 7 mg/ml crosslinked hyaluronan-cysteamine sodium salt. Hydrogel composition ID 8 comprised 3 mg/ml unmodified sodium hyaluronate (MMW 1.94 MDa), and 13 mg/ml crosslinked hyaluronan-cysteamine sodium salt.

The thiol-modified hyaluronan MMW and its degree of modification (DoM), the elastic modulus G' and the extrusion force (EF) of the sterile hydrogel composition, the MRPMW and residual thiol content of crosslinked polymer in the sterile hydrogel composition were determined as described above.

All sterile hydrogel compositions had a pH in the range of 6.7 to 7.8 and an osmolality in the range of 250 to 350 mOsm/kg

TABLE 1

Characteristics of sterile hydrogel compositions comprising crosslinked polymers with different molecular weight properties

| Hydrogel composition ID | HA-SH Polymer MMW kDa | Elastic modulus G' mPa | EF N | MRPMW kDa | DoM µmol/g | Residual thiol content µmol/g | Production method |
|---|---|---|---|---|---|---|---|
| 1* | 150 | 33,987 | 6 | 84 | 118 | 0 | B |
| 2* | 150 | 140,218 | 11 | 81 | 118 | 0 | B |
| 3* | 150 | 475,046 | 25 | n.d. | 118 | n.d. | B |
| 4* | 150 | 258,226 | 15 | n.d. | 118 | n.d. | I |
| 5 | 730 | 88,290 | 5 | 681 | 151 | 0 | A |
| 6 | 730 | 390,540 | 10 | 414 | 151 | 0 | A |
| 7 | 780 | 183,557[a] | 5 | n.d. | 149 | 1 | B |
| 8 | 780 | 817,850[a] | n.d. | n.d. | 149 | 2 | B |

An asterisk (*) indicates those examples that do not fall under the scope of the claims but are included for comparison. The abbreviation n.d. stands for "not determined".
[a]For the determination of elastic modulus G' the hydrogel composition was applied to the rheometer directly from the syringe (without needle attachment).

The formation of disulfide bonds was monitored via measuring residual thiol content of the crosslinked polymers and comparison with the initial degree of modification of the thiol-modified hyaluronan. It was found that all hydrogel compositions according to this invention had a residual thiol content of less than 15% in respect to the degree of modification of the thiol-modified hyaluronan.

Both the concentration and the MRPMW of the crosslinked polymer influenced the elastic properties of the hydrogels. Compositions comprising crosslinked polymers with a MRPMW of more than about 400 kDa (for example hydrogel composition ID 6) had increased elastic properties in comparison to compositions comprising crosslinked polymer in the same concentration but with a low MRPMW of less than 100 kDa (for example hydrogel composition ID 2). Compositions comprising crosslinked polymer in a concentration range of 9 to 13 mg/mL had increased elastic properties in comparison to compositions comprising crosslinked polymer in a concentration of 5 or 6 mg/mL, irrespective of the MRPMW of the crosslinked polymers. Comparison of the elastic modulus of hydrogel composition ID 3* and ID 8 shows that the MMW of the thiol-modified hyaluronan used for crosslinking had a positive influence on the elastic properties of the sterile composition. The thiol-modified hyaluronan of hydrogel composition ID 3* had a MMW of 150 kDa, whereas the thiol-modified hyaluronan of hydrogel composition ID 8 had a MMW of 780 kDa. Other than that, both hydrogel compositions comprised 13 mg/ml crosslinked hyaluronan-cysteamine, 3 mg/ml unmodified sodium hyaluronate and 3 mg/ml lidocaine HCl, and both hydrogel compositions were produced by the same production method.

Example 8—In Vivo Characterization of Implanted Hydrogel Compositions

Various compositions according to the invention as well as comparative compositions were investigated for the development of the mean depot volume over time after intradermal implantation via injection with magnetic resonance imaging (MRI).

Eight different sterile hydrogel compositions (see Table 1 for hydrogel characteristics) and two commercially available dermal fillers for fine line treatment, Belotero® soft (COMP1) and Profhilo® (COMP2), were tested. COMP1 contains 20 mg/mL BDDE crosslinked hyaluronan and 3 mg/mL lidocaine HCl in a phosphate buffered solution. COMP2 contains 16 mg/mL high MW hyaluronan and 16 mg/mL low MW hyaluronan in a phosphate buffered solution.

The compositions were injected intradermally into the back skin of female Sprague Dawley rats. The injection volume was about 50 µL. A maximum of 8 depots was applied per rat with a total of 12 applications per composition ID 5, ID 6, ID 7 and ID 8, 14 applications per composition ID 1, ID 2 and COMP1, 5 applications per composition ID 3 and ID 4, and 8 applications per COMP2. The volume of the intradermal hydrogel depots was monitored by MRI (Siemens Espree 1.5 T MRT device) at distinct time points for a total time period of up to 170 days. Individual depot volumes (mm$^3$) were calculated according to MRI scans and monitored over time. Calculated volumes were normalized to results obtained at Day 0 (immediately after application) and are indicated in percent (%). The mean relative depot volumes of different compositions at different time points are listed in Table 2. A certain range of days was allowed for each time point. For each hydrogel compositions, all depot volumes were determined on the same day.

TABLE 2

Development of the mean relative depot volume (%) over time

| Hydrogel composition ID | Mean relative depot volume (%) | | | | | | | | |
|---|---|---|---|---|---|---|---|---|---|
| | Day 7 | Day 14 | Day 21-24 | Day 28-30 | Day 53-56 | Day 81-84 | Day 107-112 | Day 133-140 | Day 168-170 |
| 1* | 14.1 | 0.0 | 0.0 | n.d. | n.d. | n.d. | n.d. | n.d. | n.d. |
| 2* | 27.3 | 6.9 | 0.0 | n.d. | n.d. | n.d. | n.d. | n.d. | n.d. |
| 3* | n.d. | n.d. | n.d. | 15.9 | 4.7 | n.d. | n.d. | n.d. | n.d. |
| 4* | n.d. | n.d. | n.d. | 10.1 | 0.0 | n.d. | n.d. | n.d. | n.d. |
| 5 | n.d. | n.d. | 67.6 | n.d. | 54.9 | 49.2 | 48.3 | 41.5 | 39.5 |
| 6 | n.d. | n.d. | 108.1 | n.d. | 85.7 | 85.7 | 75.8 | 75.3 | 75.9 |
| 7 | n.d. | n.d. | n.d. | 93.2 | 93.1 | 77.4 | 75.0 | 67.8 | 63.6 |
| 8 | n.d. | n.d. | n.d. | 136.7 | 114.1 | 103.7 | 98.0 | 94.5 | 85.2 |
| COMP1* | 5.2 | 0.0 | 0.0 | n.d. | n.d. | n.d. | n.d. | n.d. | n.d. |
| COMP2* | n.d. | n.d. | 0.0 | n.d. | 0.0 | 0.0 | 0.0 | 0.0 | 0.0 |

An asterisk (*) indicates those examples that do not fall under the scope of the claims but are included for comparison. The abbreviation n.d. stands for "not determined".

Comparative hydrogel compositions were degraded very quickly within less than 2 months after application. In some cases, hydrogel depots were not detectable 2 weeks (COMP1 and composition ID 1) and about 3 weeks (COMP2 and composition ID 2) after implantation. Hydrogel compositions ID 5, ID 6, ID 7 and ID 8, which were prepared by crosslinking thiol-modified hyaluronan with an initial MMW in the range of 730 to 780 kDa, showed a prolonged residence time of more than 1 month and up to 5 months. The crosslinked thiol-modified hyaluronan of hydrogel compositions ID 5 and ID 6 had a MRPMW of more than 400 kDa. Comparison of the residence time of hydrogel composition ID 3* and ID 8 shows that the MMW of the thiol-modified hyaluronan used for crosslinking had a positive influence on the residence time of the sterile composition. The thiol-modified hyaluronan of hydrogel composition ID 3* had a MMW of 150 kDa and depots of hydrogel composition ID 3* were not detectable 3 months after implantation. The thiol-modified hyaluronan of composition ID 8 had a MMW of 780 kDa and depots of hydrogel composition ID 8 were detected during the entire study period. Both hydrogel compositions were otherwise comparable; they comprised 13 mg/ml crosslinked hyaluronan-cysteamine, 3 mg/ml unmodified sodium hyaluronate and 3 mg/ml lidocaine HCl, and both compositions were produced by the same production method.

Example 9—In Vivo Characterization of Implanted Hydrogel Compositions with Different Degree of Modification and MRPMW of Crosslinked Thiol-Modified Hyaluronan Various sterile hydrogel compositions comprising crosslinked thiol-modified hyaluronan are listed in Table 3. The main difference between the compositions lies in the characteristics of the thiol-modified hyaluronan, namely in the degree of modification and the MRPMW of the crosslinked polymer. The hydrogels were produced with similar methods (compare methods B and H above). All sterile hydrogel compositions comprised crosslinked hyaluronan-cysteamine in a concentration of 17 mg/mL, 5 mg/mL unmodified sodium hyaluronate (free HA) and 3 mg/mL lidocaine HCl. The MRPMW and the residual thiol content of crosslinked polymer in the hydrogel composition and the MMW and degree of modification (DoM) of thiol-modified hyaluronan raw material were determined as described above.

TABLE 3

Characteristics of sterile hydrogel compositions comprising crosslinked polymers with different degree of modification

| Hydrogel composition ID | HA-SH Polymer MMW kDa | Elastic modulus G' mPa | MRPMW kDa | DoM µmol/g | Residual thiol content µmol/g |
|---|---|---|---|---|---|
| 9 | 628 ± 8 | 1,384,803 | 480 ± 10 | 119 | 0.88 |
| 10* | 1201 ± 15 | 714,068 | 610 ± 16 | 43 | 0.32 |
| 11 | 1335 ± 18 | 1,543,920 | 710 ± 70 | 130 | 1.06 |
| 12* | 957 ± 13 | 2,408,693 | 560 ± 19 | 350 | 4.4 |

An asterisk (*) indicates those examples that do not fall under the scope of the claims but are included for comparison.
The abbreviation n.d. stands for "not determined".

The compositions were implanted via intradermal injection into the back skin of female Sprague Dawley rats using a 25 G needle. The injection volume was about 50 µL. A maximum of 8 depots was applied per rat with 12 applications per tested composition. Degradation dynamics of the hydrogel depots were monitored via magnetic resonance imaging (MRI) on the day of application (day 0) and then at regular time intervals. Individual depot volumes (mm$^3$) were calculated according to MRI scans for each time point. Calculated volumes were normalized to results obtained at Day 0 (corresponding to 100%). The mean relative depot volume at day 84 of different hydrogel compositions is listed in Table 4.

TABLE 4

Mean relative depot volume measured on day 84 in percent.

| Hydrogel composition ID | DoM [µmol/g] | MRPMW [kDa] | Mean relative depot volume [%] at day 84 |
|---|---|---|---|
| 9 | 119 | 480 | 151.5 |
| 10* | 43 | 610 | 5.0 |
| 11 | 130 | 710 | 184.7 |
| 12* | 350 | 560 | 37.2 |

Only hydrogel compositions ID 9 and ID 11 comprising crosslinked thiol-modified hyaluronan with a DoM in the medium range (119-130 µmol/g) had a mean relative depot volume of more than 100% at day 84. Taking the higher polymer concentration of these hydrogel compositions into account, these findings correspond to the residence times measured for hydrogel compositions ID 5 and ID 6 in example 7 and example 8.

Hydrogel composition ID 10*, in which the thiol-modified hyaluronan used for crosslinking had a DoM of 43 μmol/g, was markedly degraded at day 84. The fast degradation is attributed to the low DoM (and consequently to the low degree of crosslinking), since the MRPMW was in between the values for the hydrogel compositions ID 9 and ID 11. Surprisingly, also depots of hydrogel composition ID 12* comprising crosslinked thiol-modified hyaluronan with a high DoM of 350 μmol/g (and consequently a high degree of crosslinking) were degraded by more than 60% within 12 weeks after application. Hydrogel composition ID 5, which comprised crosslinked thiol-modified hyaluronan in a concentration of 5 mg/mL outperformed this hydrogel composition in terms relative depot volume 80 days after application (see example 8).

Example 10—Formulation and Characterisation of a Sterile Hydrogel Composition

A sterile hydrogel composition comprising 11 mg/mL crosslinked HA-cysteamine, 3 mg/mL lidocaine HCl and 9 mg/mL unmodified sodium hyaluronate was produced according to method B. In brief, 1650 mg HA-cysteamine (dry weight, MMW 700 kDa, degree of modification 132 μmol/g polymer), 450 mg lidocaine HCl (dry weight) and 1350 mg sodium hyaluronate (dry weight, MW 2238 kDa) were dissolved in 130 g 10 mM phosphate buffer pH 7.1 (comprising 88 mM NaCl) under mechanical stirring at room temperature for about 17 hours. After adjustment of the pH to about pH 7.1 with 1 M sodium hydroxide solution, 10 mM phosphate buffer pH 7.1 (comprising 88 mM NaCl) was added to a final amount of 150 g composition. The solution was homogenized for about 60 min. Then, 1.2 mL of a 0.307% (v/v) hydrogen peroxide solution were added. After incubation over night at room temperature the crosslinked gel was filled into 1 mL glass syringes and sterilized via autoclavation. The sterile hydrogel composition had a pH of 6.97 and an osmolality of 266 mOsm/kg.

Degree of modification (DoM), MMW, MRPMW, extrusion force and elastic modulus G' were determined as described above and are summarized in Table 5.

TABLE 5

Characteristics of a sterile hydrogel composition

| Hydrogel composition ID | HA-SH Polymer MMW kDa | Elastic modulus G' mPa | MRPMW kDa | DoM μmol/g | EF N |
| --- | --- | --- | --- | --- | --- |
| 13 | 700 | 712,733 | 534 | 131 | 23.4 |

Example 11—Formulation and Characterisation of a Sterile Hydrogel Composition

A sterile hydrogel composition comprising 11 mg/mL crosslinked hyaluronan-cysteamine, 3 mg/mL lidocaine HCl and 5 mg/mL unmodified sodium hyaluronate was produced according to method B. In brief, 1650 mg HA-cysteamine (dry weight, MMW 700 kDa, degree of modification 132 μmol/g polymer), 450 mg lidocaine HCl (dry weight) and 750 mg sodium hyaluronate (dry weight, MW 2238 kDa) were dissolved in 130 g 10 mM phosphate buffer pH 7.1 (comprising 88 mM NaCl) under mechanical stirring at room temperature for about 17 hours. After adjustment of the pH to about pH 7.1 with 1 M sodium hydroxide solution, 10 mM phosphate buffer pH 7.1 (comprising 88 mM NaCl) was added to a final amount of 150 g composition. The solution was homogenized for about 60 min. Then, 1.2 mL of a 0.307% (v/v) hydrogen peroxide solution were added. After incubation over night at room temperature the crosslinked gel was filled into 1 mL glass syringes and sterilized via autoclavation. The sterile hydrogel composition had a pH of 6.94 and an osmolality of 252 mOsm/kg.

Degree of modification (DoM), MMW, MRPMW, extrusion force and elastic modulus G' were determined as described above and are summarized in Table 6.

TABLE 6

Characteristics of a sterile hydrogel composition

| Hydrogel composition ID | HA-SH Polymer MMW kDa | Elastic modulus G' mPa | MRPMW kDa | DoM μmol/g | EF N |
| --- | --- | --- | --- | --- | --- |
| 14 | 700 | 707,257 | 464 | 131 | 17.5 |

Example 12—Formulation and Characterisation of a Sterile Hydrogel Composition

A sterile hydrogel composition (ID 15) comprising 7 mg/ml crosslinked hyaluronan-cysteamine sodium salt (MMW 790 kDa, degree of modification 140 μmol/g), 3 mg/ml lidocaine HCl and 3 mg/ml sodium hyaluronate (MMW 2.44 MDa), 105 mM NaCl and 10 mM phosphate buffer was produced according to method B. In brief, an aqueous solution comprising HA-cysteamine sodium salt, sodium hyaluronate, lidocaine HCl and sodium chloride was prepared. Crosslinking was initiated by addition of a phosphate buffer comprising hydrogen peroxide. After 2 days incubation at room temperature the residual thiol content was measured to be less than 10% of the initial degree of modification, which indicates that more than 90% of the thiol groups of the thiol-modified hyaluronan were oxidized during the hydrogel production process. After sieving, the hydrogel was filled into syringes and sterilized at 121° C. for 15 min.

The sterile hydrogel composition had a pH of 7.08 and an osmolality of 293 mOsm/kg. The elastic modulus G' and the extrusion force were determined as described above. For the determination of elastic modulus G' the hydrogel composition was applied to the rheometer directly from the syringe (without needle attachment). The elastic modulus was 147, 877 mPa. The extrusion force was 6 N.

Example 13—Formulation and Characterisation of a Sterile Hydrogel Composition

A sterile hydrogel composition (ID 16) comprising 13 mg/mL crosslinked hyaluronan-cysteamine sodium salt (MMW 720 kDa, degree of modification 148 μmol/g), 3 mg/mL lidocaine HCl and 3 mg/mL sodium hyaluronate (MMW 1.94 MDa), 100 mM NaCl and 10 mM phosphate buffer was produced according to method B. In brief, 160 g of an aqueous solution comprising HA-cysteamine sodium salt, sodium hyaluronate, lidocaine HCl and sodium chloride were prepared by dissolving the components in 0.01 M HCl. Crosslinking was initiated by addition of 20 g of a 100 mM phosphate buffer (pH 11.9) for adjustment of the pH to 7.3, followed by addition of 20 g of a solution prepared with 19.6 μL of a 30% (v/v) hydrogen peroxide solution in 20 g water for injection. After incubation at room temperature for 22 h, the residual thiol content was measured to be 3 µmol/g, which corresponds to less than 5% of the initial degree of modification and indicates that more than 95% of the thiol groups of the thiol-modified hyaluronan were oxidized during the hydrogel production process. After sieving through a 350 µm filter plate, the hydrogel was filled into 1 ml glass syringes and sterilized via autoclavation.

The sterile hydrogel composition had a pH of 7.3 and an osmolality of 287 mOsm/kg. The elastic modulus G' and the extrusion force of the sterile hydrogel composition were determined as described above. For the determination of elastic modulus G' the hydrogel was applied to the rheometer directly from the syringe (without needle attachment). The elastic modulus was 701,583 mPa. The extrusion force was 16.4 N.

Example 14—Synthesis of Thiol Group Bearing Modification Agents

A. Preparation of bis(Glycyl)-cystamine dihydrochloride

To a mixture of cystamine dihydrochloride (1 g, 4.44 mmol) and N-(tert-Butoxycarbonyl)glycine (1.59 g, 9.10 mmol) in dry dichloromethane:THF=1:1 (20 mL) first triethylamine (1270 µL, 9.16 mmol) was added, followed by addition of a solution of EDC*HCl (1.75 g, 9.10 mmol) in dichloromethane. The reaction solution was stirred for 5 h at ambient temperature, then volatiles were evaporated under reduced pressure. The residue was taken up in ethyl acetate (250 mL) and washed with 1 n HCl (2×50 mL), half saturated NaHCO$_3$ (50 mL) and water (50 mL). The organic layer was dried over Na$_2$SO$_4$, volatiles were evaporated under reduced pressure to give the N-Boc protected bis (Glycyl)-cystamine as a colorless oil. Yield: 1.575 g (88%). $^1$H NMR (400 MHz, CDCl$_3$) δ 6.97 (s, 1H, NH), 5.53 (s, 1H, NH), 3.81 (d, J=5.8 Hz, 2H, α-CH$_2$), 3.58 (aq, J=6.3 Hz, 2H, —CH$_2$—NH—), 2.82 (t, 2H, —CH$_2$—S—), 1.45 (s, 9H, —CH$_3$ t-Bu); m/z=467.1 [M+H]$^+$, 489.1 [M+Na]$^+$.

To a solution of the N-Boc protected bis(Glycyl)-cystamine (300 mg, 0.64 mmol) in MeOH (5 mL) was added acetyl chloride (300 µL, 4.20 mmol). After the exothermic reaction had ceased, the mixture was stirred in a sealed flask for 5 h at ambient temperature, then toluene (2 mL) was added and volatiles were evaporated until the product precipitated. The white solid was isolated via suction filtration and washed with n-pentane (2×5 mL). Yield: 146 mg (67%). m.p.=184° C. (decomp.); $^1$H NMR (400 MHz, D$_2$O) δ 3.81 (s, 2H, α—CH$_2$), 3.59 (at, J=6.3 Hz, 2H, —CH$_2$—NH), 2.88 (at, 2H, —CH$_2$—S—); m/z=266.9 [M+H]$^+$, 288.9 [M+Na]$^+$.

Figure 2:
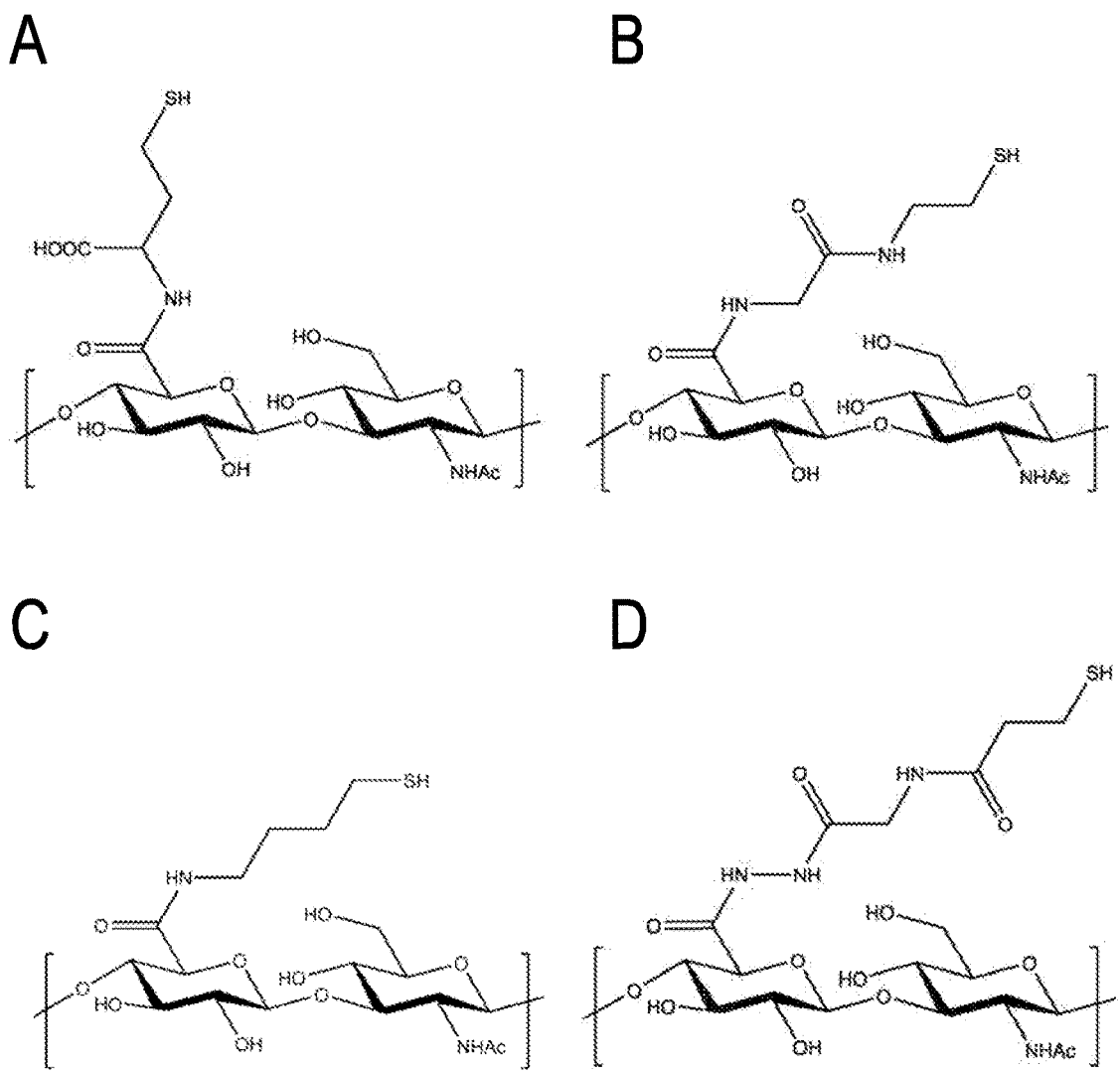
FIG. 2 shows further schematic presentations of exemplary thiol-modified hyaluronans, i.e. a hyaluronan-homocysteine substructure (A), a hyaluronan-glycyl-cysteamine substructure (B), and an N-mercapto-n-butylhyaluronamide substructure (C) and a HA-DGDTPDH substructure (D).

This modification agent allows the preparation of a hyaluronan-glycyl-cysteamine conjugate (FIG. 2 B).

B. Preparation of dithiodiethanediyldicarbonyldiamino diacetic acid dihydrazide (DGDTPDH)

To a mixture of 3,3'-dithiodipropionic acid (2 g, 9.5 mmol) and Glycine ethyl ester hydrochloride (2.66 g, 19.0 mmol) in dry dichloromethane:THF=1:1 (20 mL) was added triethylamine (2.78 µL, 20.0 mmol), followed by addition of a solution of EDC*HCl (3.83 g, 20.0 mmol) in dichloromethane. The reaction was stirred for 5 h at ambient temperature, then diluted with ethyl acetate (400 mL). The organic layer was washed with 1 n HCl (2×50 mL), half saturated NaHCO$_3$ (50 mL) and water (50 mL), then dried over Na$_2$SO$_4$ and volatiles were evaporated under reduced pressure to give dithiodiethanediyldicarbonyldiamino diacetic acid diethylester as a white solid. Yield: 1.69 g (47%); m.p.=121° C.; $^1$H NMR (400 MHz, CDCl$_3$) δ 6.50 (s, 1H, NH), 4.21 (q, J=7.1 Hz, 2H, —O—CH$_2$—), 4.04 (d, J=5.3 Hz, 2H, α—CH$_2$—N), 2.99 (t, J=7.0 Hz, 2H, —CH$_2$—S—), 2.67 (t, 2H, α—CH$_2$—CH$_2$—), 1.28 (t, 3H, —CH$_3$); m/z=381.0 [M+H]$^+$, 403.0 [M+Na]$^+$.

A mixture of the diethylester (500 mg, 1.32 mmol) and 80% aq. hydrazine hydrate (0.5 mL, 12.7 mmol) in 96% EtOH was refluxed for 5 h. The product crystallized upon cooling to ambient temperature and was collected via suction filtration and washed thoroughly with cold EtOH (2×15 mL). Yield: 335 mg (72%), white needles. m.p.=197° C. (decomp.) $^1$H NMR (400 MHz, DMSO-d6) δ 9.02 (s, 1H, —NH), 8.20 (t, J=5.7 Hz, 1H, —NH), 4.19 (s, 2H, —NH2), 3.64 (d, J=5.8 Hz, 2H, α—CH$_2$—N), 2.87 (t, J=7.2 Hz, 2H, —CH$_2$—S—), 2.53 (t, 2H, α—CH$_2$—CH$_2$—); m/z=353.1 [M+H]$^+$, 375.1 [M+Na]$^+$.

This modification agent allows the preparation a hyaluronan-2-mercapto-ethyl-carbonyl-amino-acetic acid hydrazide conjugate (FIG. 2 D).

C. Preparation of 4,4'-Dithiobis[1-butanamine]dihydrochlorid 4,4'-Dithiobis[1-butanamine] dihydrochlorid was prepared from 4-aminobutan-1-ol following protocols reported in literature (Aufort, M. et. al., ChemBioChem, 12(4), 583-592, 2011), final N-Boc deprotection was adopted and carried out with MeOH/HCl to obtain the product as dihydrochlorid salt instead: To a solution of dicarbamate (550 mg, 1.35 mmol) in methanol (6 mL) was added acetylchloride (0.6 mL, 8.4 mmol) dropwise. When the exothermic reaction had ceased, the mixture was refluxed for 5 h. Then toluene was added (6 mL) and the mixture was concentrated under reduced pressure. The crude product was repeatedly azeotroped with toluene (6 mL), then isolated via suction filtration and washed with n-pentane (2×6 mL) Yield: 340 mg (90%), white solid; m.p.=249° C. (decomp.); $^1$H NMR (400 MHz, D$_2$O+DSS) δ 3.02 (t, J=7.1 Hz, 4H, CH$_2$—N), 2.78 (t, J=6.7 Hz, 4H, —CH$_2$—S—), 1.83-1.71 (m, 8H, C—CH$_2$—CH$_2$—C). m/z=209.0 [M+H]$^+$.

This modification agent allows the preparation of an N-mercapto-n-butylhyaluronamide (FIG. 2 C).

Example 15—Formulation and Characterisation of a Sterile Hydrogel Composition Crosslinked N-mercapto-n-butylhyaluronamide A sterile hydrogel composition comprising 9 mg/mL crosslinked N-mercapto-n-butylhyaluronamide and 3 mg/mL unmodified sodium hyaluronate was produced according to method B without addition of lidocaine HCl. In brief, 450 mg N-mercapto-n-butylhyaluronamide (dry weight, MMW 767 kDa, degree of modification 98 µmol/g polymer, FIG. 2 C) and 150 mg sodium hyaluronate (dry weight, MMW 2.4 MDa) were dissolved in 44 g 0.01 M HCl (comprising NaCl) under mechanical stirring at room temperature for about 5 hours. To 41.48 g of this solution, were added 4.609 mL of 100 mM phosphate buffer pH 11.81, containing 0.015% H$_2$O$_2$, which resulted in an adjustment of the pH to about pH 7.4. The mixture was homogenized for 15 min at ambient temperature and then left over night to complete crosslinking. The crosslinked gel was filled into 1 mL glass syringes and sterilized via autoclavation. The sterile hydrogel had a pH of about 7.2 and an osmolality of 305 mOsm/kg.

Degree of modification (DoM), MMW, residual thiol content, extrusion force and elastic modulus G' of the hydrogel composition were determined as described above. For the determination of elastic modulus G' the sterile hydrogel was applied to the rheometer directly from the syringe (without needle attachment). The mean residual thiol content was 1 µmol/g and the elastic modulus G' was 252,569 mPa. The mean extrusion force was 11.9 N.

Example 16—Formulation and Characterisation of a Hydrogel Composition Comprising Crosslinked hyaluronan-glycyl-cysteamine A hydrogel composition comprising 17.9 mg/mL crosslinked hyaluronan-glycyl-cysteamine sodium salt (HA-GLYC) and 5 mg/mL unmodified sodium hyaluronate was produced according to method B without addition of lidocaine HCl. In brief, 537 mg HA-GLYC (dry weight, MMW 610 kDa, degree of modification 162 µmol/g polymer, FIG. 2 B) and 150 mg sodium hyaluronate (dry weight, MMW 2.4 MDa) were dissolved in 26 g 0.01 M HCl (comprising NaCl) under mechanical stirring at room temperature for about 5 hours. To 19.02 g of this solution, were added 2.115 mL of 100 mM phosphate buffer pH 11.85, which resulted in an adjustment of the pH to about pH 7.4. Then 273 µL of a 0.3% $H_2O_2$ solution was added and the mixture was homogenized for 15 min at ambient temperature and then left overnight for crosslinking. The crosslinked hydrogel was filled into 1 mL glass syringes and sterilized via autoclavation. The sterile hydrogel had a pH of about 7.2.

Residual thiol content, and elastic modulus G' were determined as described above. For the determination of elastic modulus G' the hydrogel was applied to the rheometer directly from the syringe (without needle attachment). The elastic modulus G' was 1,260,467 mPa. The mean residual thiol content was 0 µmol/g.

Example 17—Formulation and Characterisation of a Hydrogel Composition Comprising Crosslinked hyaluronan-homocysteine A hydrogel composition comprising 17.9 mg/mL crosslinked hyaluronan-homocysteine sodium salt (HA-HCYS) and 5 mg/mL unmodified sodium hyaluronate was produced according to method A without addition of lidocaine HCl. In brief, 537 mg HA-HCYS (dry weight, MMW 610 kDa, degree of modification 136 µmol/g polymer, FIG. 2 A) and 150 mg sodium hyaluronate (dry weight, MMW 2.4 MDa) were dissolved in 26 g 0.01 M HCl (comprising NaCl) under mechanical stirring at room temperature for about 5 hours followed by 1 hour resting time to remove air bubbles. To 23.68 g of the solution, 2.63 ml 100 mM phosphate buffer pH 12.04 was added, which resulted in an adjustment of the pH of the solution to about pH 7.2. The mixture was left for 48 h at room temperature for crosslinking, then the crosslinked hydrogel was filled into 1 mL glass syringes and sterilized via autoclavation. The sterile hydrogel had a pH of about 7.0.

Residual thiol content and elastic modulus G' were determined as described above. For the determination of elastic modulus G' the hydrogel was applied to the rheometer directly from the syringe (without needle attachment). The elastic modulus G' was 1,759,900 mPa The mean residual thiol content was 0 µmol/g.

Example 18—Formulation and Characterisation of a Hydrogel Composition Comprising Crosslinked hyaluronan-2-mercapto-ethyl-carbonyl-amino-acetic acid hydrazide A hydrogel comprising 17.9 mg/mL crosslinked hyaluronan-2-mercapto-ethyl-carbonyl-amino-acetic acid hydrazide sodium salt (HA-DGDTPDH) and 5 mg/mL unmodified sodium hyaluronate was produced according to method B without addition of lidocaine HCl. In brief, 537 mg HA-DGDTPDH (dry weight, MMW 770 kDa, degree of modification 134 µmol/g polymer, FIG. 2 D) and 150 mg sodium hyaluronate (dry weight, MMW 2.4 MDa) were dissolved in 26 g 0.01 M HCl (comprising 192 mg NaCl) under mechanical stirring at room temperature for about 5 h. To 20.20 g of this solution, 2.25 ml 100 mM phosphate buffer pH 12.07, containing 0.041% $H_2O_2$ was added, which resulted in an adjustment of the pH of the solution to about pH 7.0. The mixture was left for 18 h at room temperature for crosslinking. The crosslinked hydrogel was then filled into 1 mL glass syringes and sterilized via autoclavation. The sterile hydrogel had a pH of about 7.0 and an osmolality of 326 mOsm/kg.

Residual thiol content and elastic modulus G' were determined as described above. For the determination of elastic modulus G' the hydrogel was applied to the rheometer directly from the syringe (without needle attachment). The elastic modulus G' was 698,860 mPa. The mean residual thiol content was 0 µmol/g.

The invention claimed is:

1. A sterile hydrogel composition comprising:
a crosslinked polymer,
wherein the crosslinked polymer is an oxidation product of a thiol-modified hyaluronan,
wherein the thiol-modified hyaluronan has a degree of modification with thiol groups of more than about 80 µmol per gram polymer,
wherein the thiol-modified hyaluronan has a degree of modification with thiol groups of less than about 280 µmol per gram polymer, and
wherein the thiol-modified hyaluronan has a mean molecular weight of at least 400 kDa.

2. The composition according to claim 1, wherein the crosslinked polymer has a mean reduced post-sterilisation molecular weight of more than about 250 kDa, wherein the mean reduced post-sterilisation molecular weight is defined as the mean molecular weight of a reduced thiol-modified hyaluronan from said sterile hydrogel composition after exposing said crosslinked polymer to reductive conditions.

3. The composition according to claim 1, wherein the thiol-modified hyaluronan is comprised in the composition with a concentration of at most 14 mg/mL.

4. The composition according to claim 1, wherein the thiol-modified hyaluronan is comprised in the composition with a concentration of at least 3 mg/ml.

5. The composition according to claim 1, wherein the composition further comprises a local anaesthetic agent.

6. The composition according to claim 1, wherein the thiol-modified hyaluronan is a conjugate of a modification agent linked to hyaluronan via an amide bond, wherein the agent is selected from the group comprising glutathione, aminoalkylthiols comprising a $C_2$-$C_6$-linear or branched alkyl chain, cysteine, homocysteine, amino acid derivatives of cysteamine, cysteine and homocysteine, carboxylate esters of homocysteine and carboxylate esters of cysteine.

7. The composition according to claim 1, wherein the thiol-modified hyaluronan is a hyaluronan-cysteamine conjugate (HA-cysteamine).

8. The composition according to claim 1, wherein the composition further comprises an unmodified hyaluronan.

9. The composition according to claim 1, wherein the composition has a residual thiol content of less than 20% in respect to the degree of modification of the thiol-modified hyaluronan.

10. The composition according to claim 1, wherein the composition has a specific extrusion force of 30 N or lower, wherein the specific extrusion force is measured during extrusion of the composition from a standard 1 mL glass syringe with a hypodermic needle by a lumen measured in Gauge (G) of 30 G at an extrusion rate of 12 mm/min.

11. A medicine comprising the composition according to claim 1.

12. The composition according to claim 1, wherein the thiol-modified hyaluronan has a degree of modification with thiol groups of more than about 105 μmol per gram polymer.

13. The composition according to claim 1, wherein the thiol-modified hyaluronan has a degree of modification with thiol groups of more than about 120 μmol per gram polymer.

14. The composition according to claim 1, wherein the thiol-modified hyaluronan has a degree of modification with thiol groups of less than about 240 μmol per gram polymer.

15. The composition according to claim 1, wherein the thiol-modified hyaluronan has a degree of modification with thiol groups of less than 200 μmol per gram polymer.

16. The composition according to claim 1, wherein the thiol-modified hyaluronan has a mean molecular weight of at least 500 kDa.

17. The composition according to claim 1, wherein the thiol-modified hyaluronan has a mean molecular weight of at least 600 kDa.

18. The composition according to claim 3, wherein the thiol-modified hyaluronan is comprised in the composition with a concentration of at most 12 mg/mL.

19. The composition according to claim 3, wherein the thiol-modified hyaluronan is comprised in the composition with a concentration of at most 10 mg/ml.

20. The composition according to claim 4, wherein the thiol-modified hyaluronan is comprised in the composition with a concentration of at least 4 mg/mL.

21. The composition according to claim 5, wherein the local anaesthetic agent comprises lidocaine.

22. The composition according to claim 9, wherein the residual thiol content is less than 15%.

* * * * *